US007767453B2

(12) United States Patent
Zhang et al.

(10) Patent No.: US 7,767,453 B2
(45) Date of Patent: Aug. 3, 2010

(54) CULTURED HEMATOPOIETIC STEM CELLS AND METHOD FOR EXPANSION AND ANALYSIS THEREOF

(75) Inventors: Chengcheng Zhang, Arlington, MA (US); Harvey Lodish, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 949 days.

(21) Appl. No.: 11/255,191

(22) Filed: Oct. 20, 2005

(65) Prior Publication Data

US 2006/0115898 A1 Jun. 1, 2006

Related U.S. Application Data

(60) Provisional application No. 60/620,509, filed on Oct. 20, 2004.

(51) Int. Cl.
  *C12N 5/00* (2006.01)
(52) U.S. Cl. ............... 435/375; 435/325; 435/355; 435/377
(58) Field of Classification Search .............. None
  See application file for complete search history.

(56) References Cited

U.S. PATENT DOCUMENTS

| 2002/0177227 | A1 | 11/2002 | Kraus et al. ........... 435/366 |
| 2004/0157326 | A1 | 8/2004 | Miura et al. |
| 2005/0032122 | A1 | 2/2005 | Hwang et al. |
| 2005/0276793 | A1 | 12/2005 | Milhem et al. |

FOREIGN PATENT DOCUMENTS

| EP | 0 962 530 A2 | 12/1999 |
| EP | 1 308 511 A1 | 5/2003 |
| WO | WO 00/52167 | 9/2000 |
| WO | 02/083845 | 10/2002 |

OTHER PUBLICATIONS

Huang et al. Blood 1994;83:1515-26.*
Rossi et al. Stem Cells Dev Aug. 2004;13:362-71.*
DiFalco et al. Biochem J 1997;326:407-13.*
Miyagawa et al. Brit J Haematol 2000;109:555-62.*
Smith et al. Curr Protoc Immunol. May 2001;Chapter 6:Unit 6.17.*
Schwartz et al. J Immunol 1997;159:895-904.*
Ooman et al. Exp Hematol 2002;30:116-25.*
Dawczynski, K., et al. "Changes of serum growth factors (IGF-I,-II and IGFBP-2,-3) prior to and after stem cell transplantation in children with acute leukemia," *Bone Marrow Transplantation*, vol. 32, pp. 411-415 (2003).
Huynh, H., et al., "Insulin-like growth factor-binding protein 2 secreted by a tumorigenic cell line supports ex vivo expansion of mouse hematopoietic stem cells." *Stem Cells* (Miamisburg), vol. 26, pp. 1628-1635 (2008).
Liu, L., et al., "Functional cloning of IGFBP-3 from human microvascular endothelial cells reveals its novel role in promoting proliferation of primitive CD34+CD38-hematopoietic cells in vitro." *Oncology Research*, vol. 13, pp. 359-371 (2003).
Zhang, C., et al., "Angiopoietin-like 5 and IGFBP2 stimulate ex vivo expansion of human cord blood hematopoietic stem cells as assayed by NOD/SCID transplantation." *Blood*, vol. 111, pp. 3415-3423 (2008).
Antonchuk, J. et al., "HOXB4-Induced Expansion of Adult Hematopoietic Stem Cells Ex Vivo," *Cell*, vol. 109, pp. 39-45 (2002).
Arai, F. et al., "Tie2/Angiopoietin-1 Signaling Regulates Hematopoietic Stem Cell Quiescence in the Bone Marrow Niche," *Cell*, vol. 118, pp. 149-161 (2004).
Baumann, C.I. et al, "PECAM-1 is expressed on hematopoietic stem cells throughout ontogeny and identifies a population of erythroid progenitors," *Blood*, vol. 104, No. 4, pp. 1010-1016 (2004).
Bunting, K.D. et al., "Effects of Retroviral-Mediated MDR1 Expression on Hematopoietic Stem Cell Self-Renewal and Differentiation in Culture," *Ann. N.F. Acad. Sci.*, vol. 872, pp. 125-140 (1999).
Chen, C.Z. et al., "The Endoglin $^{Positive}$Sca-1 $^{Positive}$ Rhodamine $^{Low}$ Phenotype Defines a near-Homogeneous Population of Long-Term Repopulating Hematopoietic Stem Cells," *Immunity*, vol. 19, pp. 525-533 (2003).
de Haan, G. et al., "In Vitro Generation of Long-Term Repopulating Hematopoietic Stem Cells by Fibroblast Growth Factor-1," *Developmental Cell*, vol. 4, pp. 241-251 (2003).
Devine, S.M. et al., "Clinical application of hematopoietic progenitor cell expansion: current status and future prospects," *Bone Marrow Transplantation*, 31, pp. 241-252 (2003).
Domen, J. et al., "Self-renewal, differentiation or death: regulation and manipulation of hematopoietic stem cell fate," *Molecule Medicine Today*, vol. 5, pp. 201-208 (1999).
Fraser, C.C. et al., "Expansion In vitro of Retrovirally Marked Totipotent Hematopoietic Stem Cells," *Blood*, vol. 76, No. 6, pp. 1071-1076 (1990).
Goodell, M.A., et al., "Isolation and Functional Properties of Murine Hematopoietic Stem Cells that are Replicating In Vivo," *J. Exp. Med.*, vol. 183, pp. 1797-1806 (1996).
Henniker, A.J., "CD24," *J. Biol Regulators and Homeostatic Agents*, 15, pp. 182-184 (2001).
Kondo, M. et al., "Biology of Hematopoietic Stem Cells and Progenitors: Implications for Clinical Application," *Annu. Rev. Immunol.*, 21, pp. 759-806 (2003).
Li, C.L. et al., "Stem Cell Factor Enhances the Survival But Not the Self-Renewal of Murine Hematopoietic Long-Term Repopulating Cells," *Blood*, vol. 84, No. 12, pp. 408-414 (1994).
Matsunaga, T. et al., "Thrombopoietin Promotes the Survival of Murine Hematopoietic Long-Term Reconstituting Cells; Comparison With the Effects of FLT3/FLK-2 Ligand and Interleukin-6," *Blood*, vol. 92, No. 2, pp. 452-461 (1998).
Miller, C.L. et al., "Expansion in vitro of adult murine hematopoietic stem cells with transplantable lmph-myeloid reconstituting ability," *Proc. Natl. Acad. Sci., USA*, vol. 94, pp. 13648-13653 (1997).

(Continued)

Primary Examiner—Q. Janice Li
(74) Attorney, Agent, or Firm—Proskauer Rose LLP

(57) ABSTRACT

Hematopoietic stem cells and methods for ex vivo expansion of hematopoietic stem cells are provided. The methods comprise culturing the cells in a media containing an effective amount insulin-like growth factor (IGF), fibroblast growth factor (FGF), thrombopoietin (TPO), and stem cell factor (SCF), under conditions sufficient for expansion of said cells. Methods for identifying expanded hematopoeitc stem cells and kits for ex vivo expansion of hematopoietic stem cells are also provided.

27 Claims, 14 Drawing Sheets

OTHER PUBLICATIONS

Miyagi, T. et al., "Flk1+ cells derived from mouse embryonic stem cells reconstitute hematopoiesis in vivo in SCID mice," *Exper. Hematology*, vol. 30, pp. 1444-1453 (2002).

Moore, K.A. et al., "In Vitro Maintenance of Highly Purified, Transplantable Hematopoietic Stem Cells," *Blood*, vol. 89, No. 12, pp. 4337-4347 (1997).

Moore, T. et al., "Expression of CD43 on Murine and Human Pluripotent Hematopoietic Stem Cells[1]," *The Journal of Immunology*, 153, pp. 4978-4987 (1994).

Orschell-Traycoff, C.M. et al., "Homing and engraftment potential of Sca-1+ in cells fractionated on the basis of adhesion molecule expression and position in cell cycle," *Blood*, vol. 96, No. 4, pp. 1380-1387 (2000).

Osawa, M. et al., "Long-Term Lymphohematopoietic Reconstitution by a Single C34-Low/Negative Hematopoietic Stem Cell," *Science*, vol. 273, No. 5272, pp. 242-245 (1996).

Peled, A. et al., "Dependence of Human Stem Cell Engraftment and Repopulation of NOD/SCID Mice on CXCR4," *Science*, vol. 283, pp. 845-848 (1999).

Reya, T. et al., "A role for Wnt signaling in sef-renewal of haematopoietic stem cells," *Nature*, 423, pp. 409-414 (2003).

Sato, T. et al., "Reversible Expression of CD34 by Murine Hematopoietic Stem Cells" *Blood*, vol. 94, No. 8, pp. 2548-2554 (1999).

Shizuru, J.A., et al., "Hematopoietic Stem and Progenitor Cells; Clinical and Preclinical Regeneration of the Hematolymphoid System," *Annu. Rev. Med.*, 56, pp. 509-538 (2005).

Sitnicka, E. et al., "The effect of Thrombopoietin on the Proliferation and Differentiation of Murine Hematopoietic Stem Cells," *Blood*, vol. 87, No. 12, pp. 4998-5005 (1996).

Solar, G.P. et al., "Role of c-mpl in Early Hematopoiesis," *Blood*, vol. 92, No. 1, pp. 4-10 (1998).

Spangrude, G.J. et al., "Purification and Characterization of Mouse Hematopoietic Stem Cells," *Science*, vol. 241, No. 4861, pp. 58-62 (1988).

Varnum-Finney, B. et al., "Pluripotent, cytokine-dependent, hematopoietic stem cells are immortalized by constitutive Notch 1 signaling," *Nature Medicine*, vol. 6, No. 11, pp. 1278-1281 (2000).

Yagi, M. et al., "Sustained ex vivo expansion of hematopoietic stem cells mediated by thrombpoietin," *Proc. Natl. Acad. Sci. USA*, vol. 96, pp. 8126-8131 (1999).

Yin, A. et al., "AC133, a Novel Marker for Human Hematopoietic Stem and Progenitor Cells," *Blood*, vol. 90, No. 12, pp. 5002-5012 (1997).

Zhang, C.C., et al., "Insulin-like growth factor 2 expressed in a novel fetal liver cell for hematopoietic stem cells," *Blood*, vol. 103, No. 7, pp. 2513-2521 (2004).

Zhang, C.C., et al., "Murine hematopoietic stem cells change their surface phenotype during ex vivo expansion," *Blood*, vol. 105, No. 11, pp. 4314-4320 (2005).

Breems et al., "Frequency Analysis of Human Primitive Haematopoietic Stem Cell Subsets Using a Cobblestone Area Forming Cell Assay," *Leukemia*, 8;1095-1104 (1994).

Camargo, F.D. et al., "Single Hematopietic Stem Cells Generate Skeletal Muscle Through Myeloid Intermediates," *Nat Med*, 9:1520-7 (2003).

Camenisch, G. et al., "ANGPTL3 Stimulates Endothelial Cell Adhesion and Migration via Integrin $\alpha_v\beta_3$ and Induces Blood Vessel Formation in Vivo," *The Journal of Biological Chemistry*, vol. 277, No. 19, pp. 17281-17290 (2002).

Cipolleschi, M.G. et al., "The Role of Hypoxia in the Maintenance of Hematopoietic Stem Cells," *Blood*, vol. 82, No. 7, pp. 2031-2037 (1993).

Conklin, D. et al., "Identification of a Mammalian Angiopoietin-Related Protein Expressed Specifically in Liver," *Genomics*, 62;477-82 (1999).

Craig, W. et al., "Expression of Thy-1 on Human Hematopoietic Progenitor Cells," *J. Exp. Med.*, vol. 177, pp. 1331-1342 (1993).

Cwirla et al., "Peptide Agonist of the Thrombopoietin Receptor as Potent as the Natural Cytokine,"*Science*, 276:1696-1699 (1997).

Gussoni, E. et al., "Dystrophin Expression in the Mdx Mouse Restored by Stem Cell Transplantation," *Nature*, 401:390-394 (1999).

Issaragrisil, S. et al., "Brief Report: Transplantation of Cord-Blood Stem Cells into a Patient with a Severe Thalassemia," *The New England Journal of Medicine*, vol. 332, No. 6, pp. 367-369 (1995).

Kim, I. et al., "Molecular Cloning, Expression, and Characterization of Angiopoietin-Related Protein," *The Journal of Biological Chemistry*, vol. 274, No. 37, pp. 26523-26528 (1999).

Koishi, R. et al., "Angptl3 Regulates Lipid Metabolism in Mice," *Nat Genet*, 30:151-7 (2002).

Krosi, J. et al., "In Vitro Expansion of Hematopoietic Stem Cells by Recombinant TAT-HOXB4 Protein," *Nat Med*, 9:1428-32 (2003).

Kyoizumi et al., "Implantation and Maintenance of Functional Human Bone Marrow in SCID-hu Mice," *Blood*, 79:1704-1711 (1992).

Murray et al., "Enrichment of Human Hematopoietic Stem Cell Activity in the CD34+Thy-1+Lin Subpopulation from Mobilized Peripheral Blood," *Blood*, 85:368-378 (1995).

Oike et al., "Angiopoietin-Related/Angiopoietin-Like Proteins Regulation Angiogenesis," *Int. J. Hematol.*, 841:21-28 (2004).

Owen, M., "Marrow Derived Stromal Stem Cells," *J. Cell Science Supp.*, 10:63-76 (1988).

Pittenger, M.F. et al., "Mesenchymal Stem Cells of Human Adult Bone Marrow," *Cold Spring Harbor, New York: Cold Spring Harbor Laboratory Press*, 349-374 (2001).

Shi, Q. et al., "Evidence for Circulating Bone Marrow-Derived Endothelial Cells," *Blood*, vol. 92, No. 2, pp. 362-367 (1998).

Sorentino, B.P., "Clinical Strategies for Expansion of Hematopoietic Stem Cells," *Nat Rev Immunol*, 4:787-88 (2004).

Spangrude, G.J. et al., "Purification and Characterization of Mouse Hematopoietic Stem Cells," *Science*, vol. 241, No. 4861, pp. 58-62 (1988).

Srour et al., "Animal Models for Human Hematopoiesis," *J. Hematother.*, 1:143-153 (1992).

Sutherland, H.J. et al., "Functional Characterization of Individual Human Hematopoietic Stem Cells Structured at Limiting Dilution on Supportive Marrow Stromal Layers," *Proc. Natl. Acad. Sci. USA*, vol. 87, pp. 3584-3588 (1990).

Valenzuela, D.M. et al., "Angiopoietins 3 and 4: Diverging Gene Counterparts in Mice and Humans," *Proc. Natl. Acad. Sci. USA*, vol. 96, pp. 1904-1909 (1999).

Willert, J. et al., "Wnt Proteins are Lipid-Modified and Can Act as Stem Growth Factors," *Nature*, 423:448-52 (2003).

Zanjani et al., "Engraftment and Long-Term Expression of Human Fetal Hemopoietic Stem Cells in Sheep Following Transplantation in Utero," *J. Clin. Invest.*, 89:1178-1188 (1992).

Zeng, L. et al., "Identification of a Novel Human Angioprotein-Like Gene Expressed Mainly in Heart," *J Hum Genet*, 48:159-62 (2003).

International Search Report for PCT/US2005/037960 (4 pgs.).

Chen, Chang-Zheng, et al., "Identification of endoglin as a functional marker that defines long-term repopulating hematopoietic stem cells," *Proceedings of the National Academy of Sciences of the United States of America*, vol. 99, No. 24, pp. 15468-15473 (2002).

Choong, Meng Ling, et al., "A novel role for proliferin-2 in the ex vivo expansion of hematopoietic stem cells," *FEBS Letters*, vol. 550, pp. 155-162 (2003).

Zhang, Cheng Cheng, et al., "Angiopoietin-like proteins stimulate ex vivo expansion of hematopoietic stem cells," *Nature Medicine*, vol. 12, No. 2, pp. 240-245 (2006).

International Search Report for International Application No. PCT/US2006/020078 date of mailing Apr. 12, 2006.

\* cited by examiner

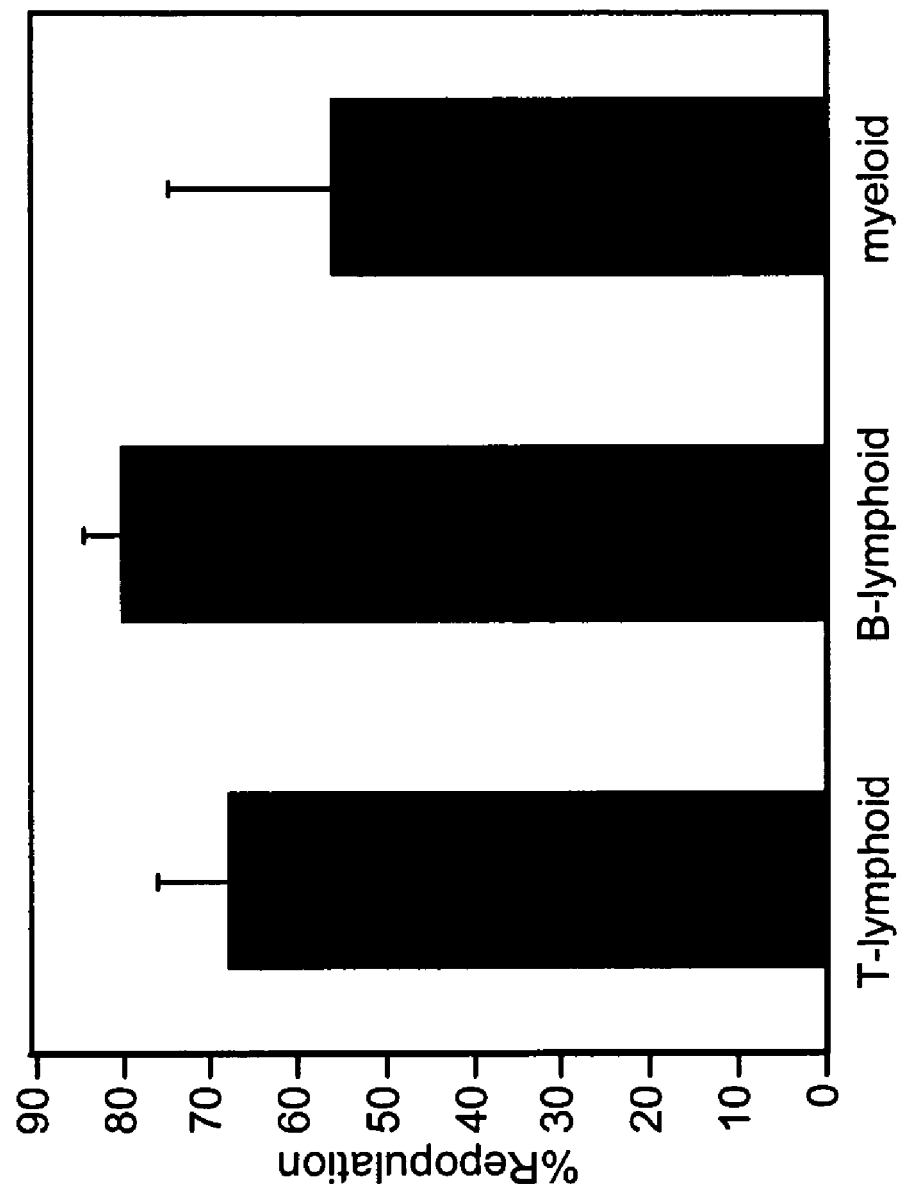

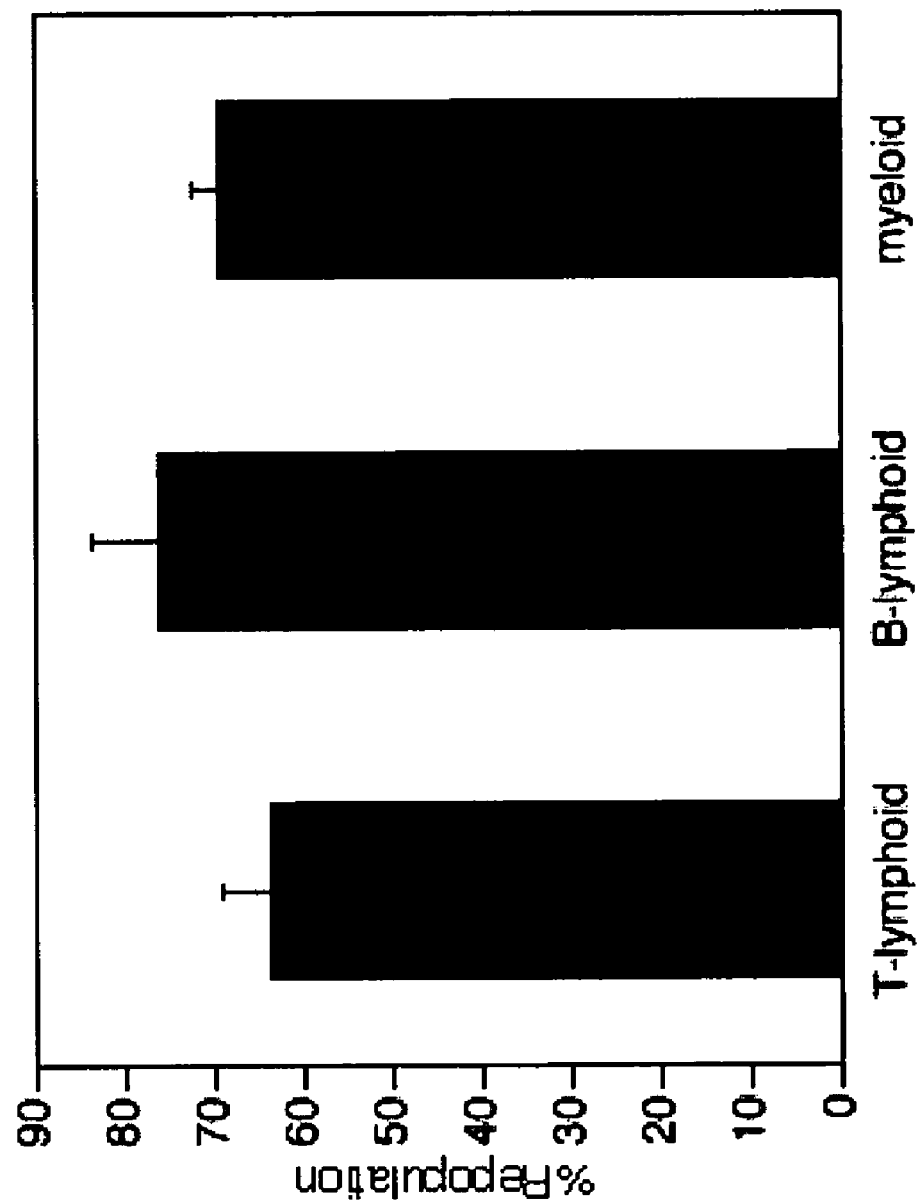

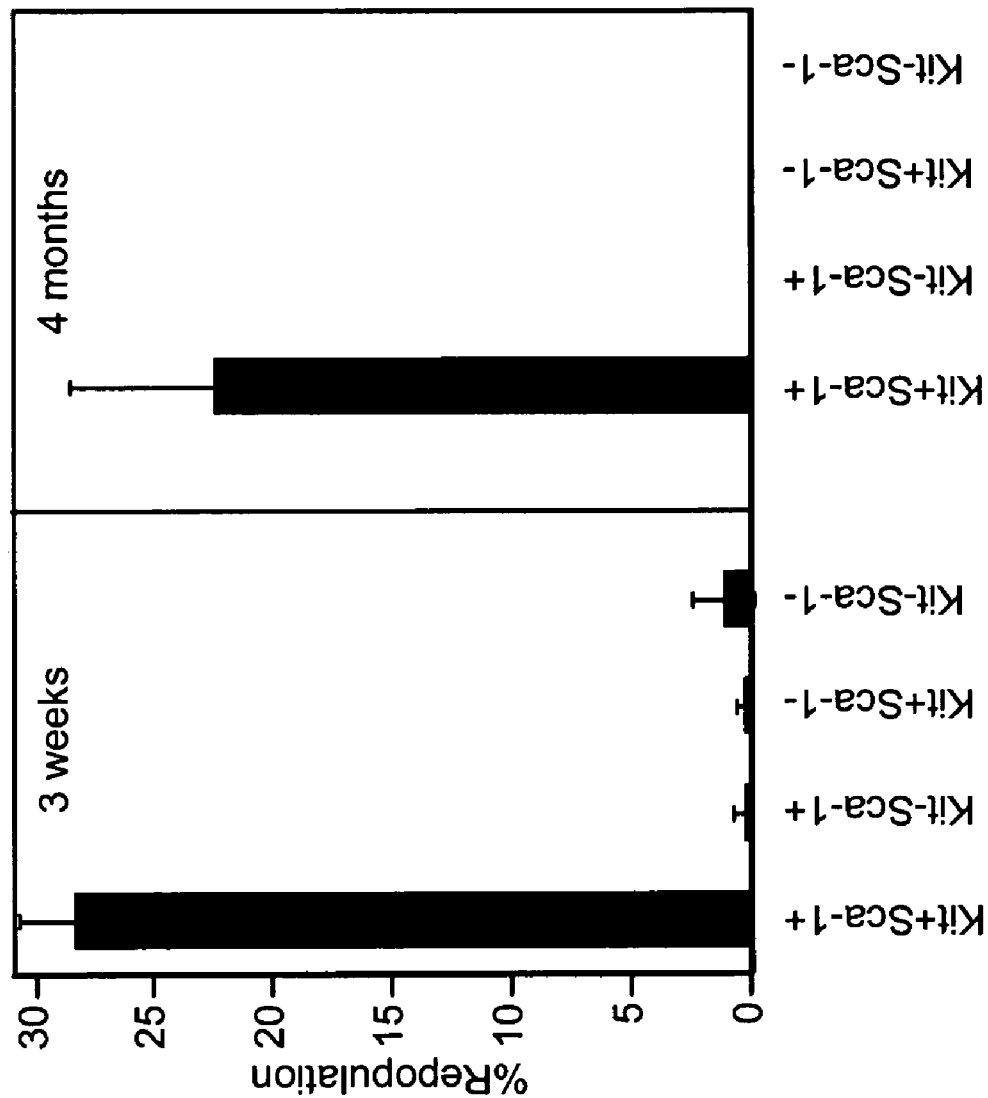

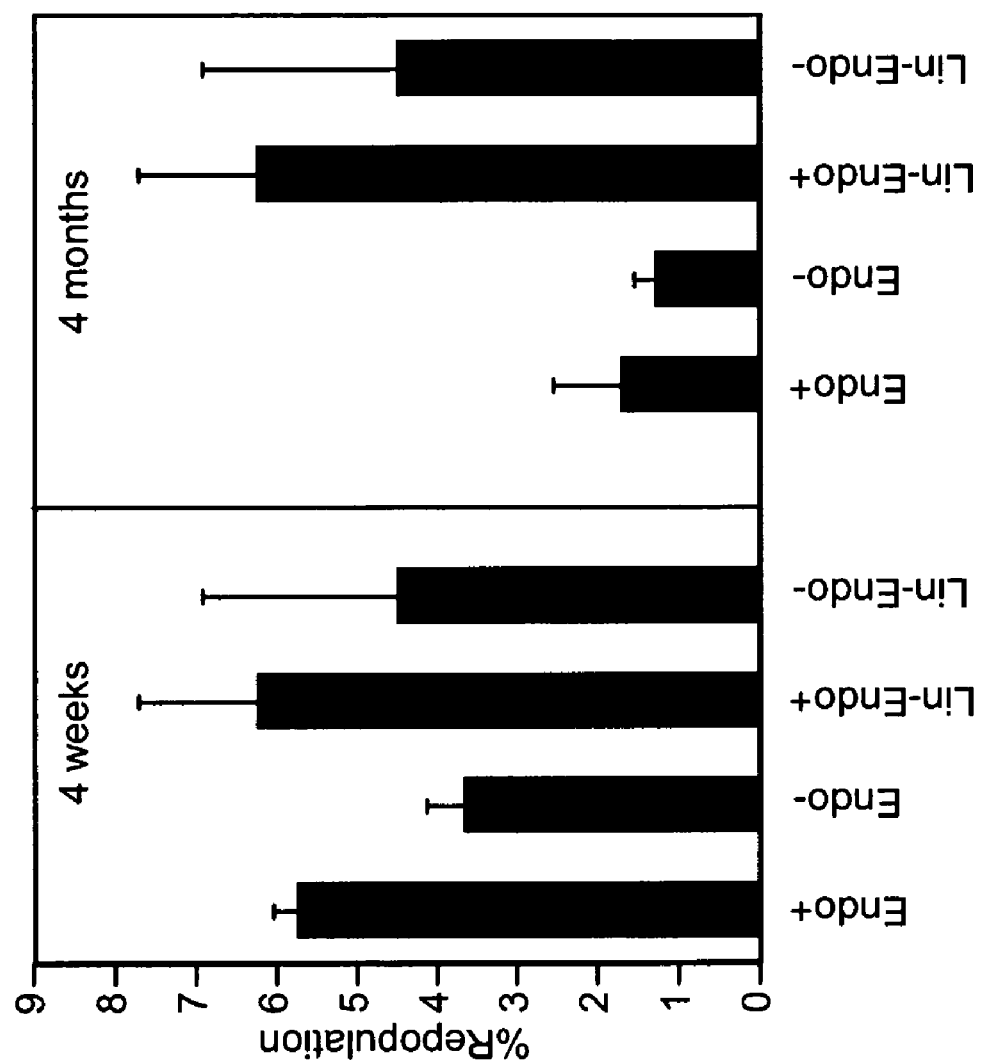

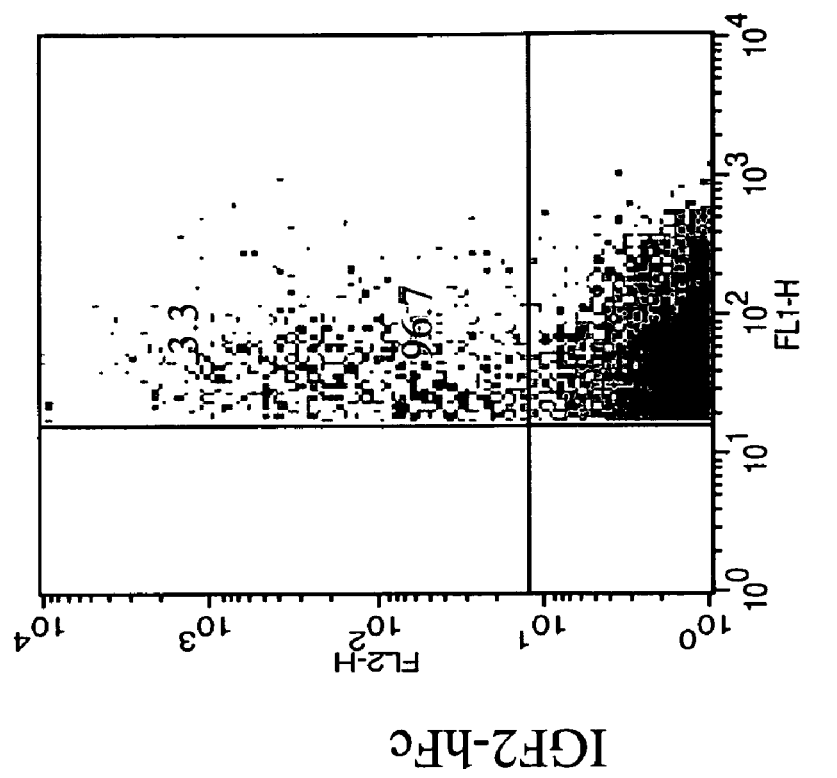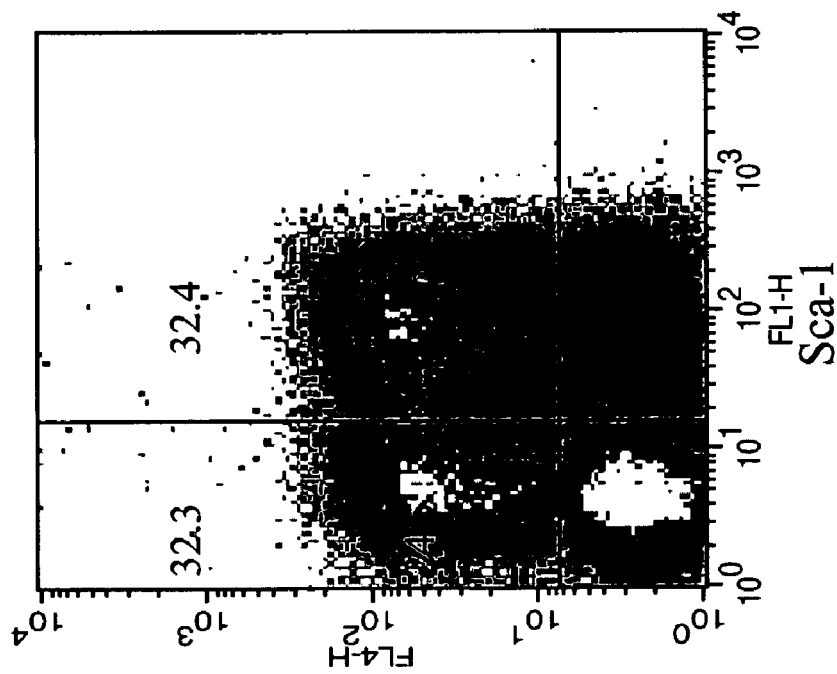
Fig 7A

CULTURED HEMATOPOIETIC STEM CELLS AND METHOD FOR EXPANSION AND ANALYSIS THEREOF

RELATED APPLICATIONS

This application claims the benefit of and priority to U.S. provisional application No. 60/620,509, filed Oct. 20, 2004, the teachings of which are incorporated herein in their entirety.

GOVERNMENT FUNDING

This invention was supported by the National Science Foundation under grant No. EEC 9843342. The government has certain rights to the invention.

FIELD OF INVENTION

The present application is directed to cultured hematopoietic stem cells, the expansion of hematopoietic stem cells ex vivo, and the identification of hematopoietic stem cells from a culture of other hematopoietic cells.

BACKGROUND OF THE INVENTION

The hematopoietic stem cell (HSC) through proliferation and differentiation gives rise to most, if not all, of the cells in the hematopoietic system. Thus, HSCs are ideal candidates for disease therapy and are attractive target cells for delivery of genes and gene products to a host animal. However, it is often difficult to isolate sufficient HSCs from tissue such as bone marrow for a number of reasons. The number of HSCs in the tissue can be low compared to non-HSCs and the correct identification of HSCs capable of repopulating the bone marrow of a host animal has been difficult and inconsistent. Difficulties in ex vivo expansion of hematopoietic stem cells (HSCs) have greatly hampered their clinical utility as well as studies of their biological properties (J. Domen, I. L. Weissman, Mol Med Today 5, 201-8 (May, 1999)). Although numerous attempts have been made to increase the number of long-term HSCs (LT-HSCs) in culture, there has only been limited success. The use of stromal cell lines and combinations of cytokines have, at best, lead to maintenance or modest expansion of murine long-term (LT)-HSC activity (K. A. Moore, H. Ema, I. R. Lemischka, Blood 89, 4337-47 (Jun. 15, 1997); C. C. Fraser, C. J. Eaves, S. J. Szilvassy, R. K. Humphries, Blood 76, 1071-6 (Sep. 15, 1990); and C. L. Miller, C. J. Eaves, Proc Natl Acad Sci USA 94, 13648-53 (Dec. 9, 1997)). The introduction of exogenous transcription factors can significantly expand HSCs (K. D. Bunting, J. Galipeau, D. Topham, E. Benaim, B. P. Sorrentino, Ann N Y Acad Sci 872, 125-40; discussion 140-1 (Apr. 30, 1999); B. Varnum-Finney et al., Nat Med 6, 1278-81 (November, 2000); J. Antonchuk, G. Sauvageau, R. K. Humphries, Cell 109, 39-45 (Apr. 5, 2002); and T. Reya et al., Nature 423, 409-14 (May 22, 2003)), but this approach may have undesirable outcomes for recipients. Furthermore, it appears that in vivo HSC surface phenotypes do not correlate to expansion of HSC activity (K. D. Bunting, J. Galipeau, D. Topham, E. Benaim, B. P. Sorrentino, Ann N Y Acad Sci 872, 125-40; discussion 140-1 (Apr. 30, 1999)). Therefore, the in vivo stem cell phenotype does not necessarily predict the hematopoietic repopulating potential of the ex vivo cultured cells.

There is a need, therefore, for improved methods of ex vivo cell culture systems capable of expanding hematopoietic cells that maintain pluripotency. Furthermore, there is a need for methods that allow the identification of ex vivo expanded cells that retain such pluripotency.

SUMMARY

We have developed methods for propagating hematopoietic stem cells while retaining pluripotency. The methods comprise culturing a population of cells in a medium containing an effective amount of insulin-like growth factor (IGF) and at least one factor selected from the group consisting of fibroblast growth factor (FGF), thrombopoietin (TPO), or stem cell factor (SCF), under conditions sufficient for expansion of hematopoietic stem cells. The population of cultured cells comprises cells obtained from tissue that includes or is expected to include HSCs. In one embodiment, the population of cells comprises bone marrow cells. The population of cells can also comprise a sub-population of cells enriched for HSCs. For example, the population of cells can comprise "side population" (SP) cells as described below. Other sub-populations of cells from host tissue that contain hematopoietic stem cells can be used.

The present invention also includes hematopoietic stem cells. In one embodiment, the hematopoietic stem cells of the present invention are produced by the method of the present invention. In one embodiment, the hematopoietic stem cells of the present invention have a surface phenotype of Sca-1+, IFG-2 receptor+, Kit+, CD31+, PrP−, and Tie-2−.

Methods for identifying hematopoietic stem cells that retain at least some HSC activity are also provided. The methods comprise characterizing surface phenotype of cultured cells. In one embodiment, a surface phenotype of Sca-$1^+$, IGF-2 receptor$^+$, Kit$^+$, CD31$^+$ and one or more of the group consisting of PrP$^-$, Tie-2$^-$, CD62L$^-$, prominin-1$^-$, CD34$^-$, CD38$^-$ and Lin$^-$ is indicative of a hematopoietic stem cell. In another embodiment, a surface phenotype of Sca-1$^+$, IGF-2 receptor$^+$, Kit$^+$, CD31$^+$ and two or more of the group consisting of PrP$^-$, Tie-2$^-$, CD62L$^-$, prominin-1$^-$, CD34$^-$, CD38$^-$, and Lin$^-$ is indicative of a hematopoietic stem cell. In another embodiment, a surface phenotype of Sca-1$^+$, IGF-2 receptor$^+$, Kit$^+$, CD31$^+$ and of three or more of the group consisting PrP$^-$, Tie-2$^-$, CD62L$^-$, prominin-1$^-$, CD34$^-$, CD38$^-$, and Lin$^-$ is indicative of a hematopoietic stem cell. In still another embodiment, a surface phenotype of Sca-1$^+$, IGF-2 receptor$^+$, Kit$^+$, CD31$^+$, PrP$^-$, Tie-2$^-$, CD62L$^-$, prominin-1$^-$, CD38$^-$, and Lin$^-$ is indicative of a hematopoietic stem cell.

Kits for propagating or expanding hematopoietic stem cells ex vivo are also provided. In one embodiment, the kit comprises at least one factor selected from the group consisting of IGF-2, SCF, TPO, and FGF-1 and instructions for expanding hematopoietic stem cells ex vivo. In another embodiment, the kit comprises two of the factors from the group consisting of IGF-2, SCF, TPO, and FGF-1. In another embodiment, the kit comprises each of IGF-2, SCF, TPO, and FGF-1.

BRIEF DESCRIPTION OF FIGURES

FIG. 1C shows a chart of lineage contribution at 4 months post-transplant.

FIG. 1D shows a chart of lineage contribution at 3 months post-transplant of secondary transplanted mice.

FIG. 3B is a chart showing % repopulation 3 weeks and 4 months after transplant with cells having the indicated phenotype, demonstrating that ex vivo expanded HSCs are Sca-$1^+$ and Kit$^+$ FIG. 4 is a chart showing % repopulation 4 weeks and 4 months after transplant with cells having the indicated phenotype, demonstrating that ex vivo expanded bone marrow HSCs are in both Endoglin – and + fractions.

FIG. 7A shows a FACS analysis demonstrating that cultured Lin$^-$Sca-1$^+$PrP$^-$CD62L$^-$ cells enriched for HSCs.

DETAILED DESCRIPTION

Figure 1A:
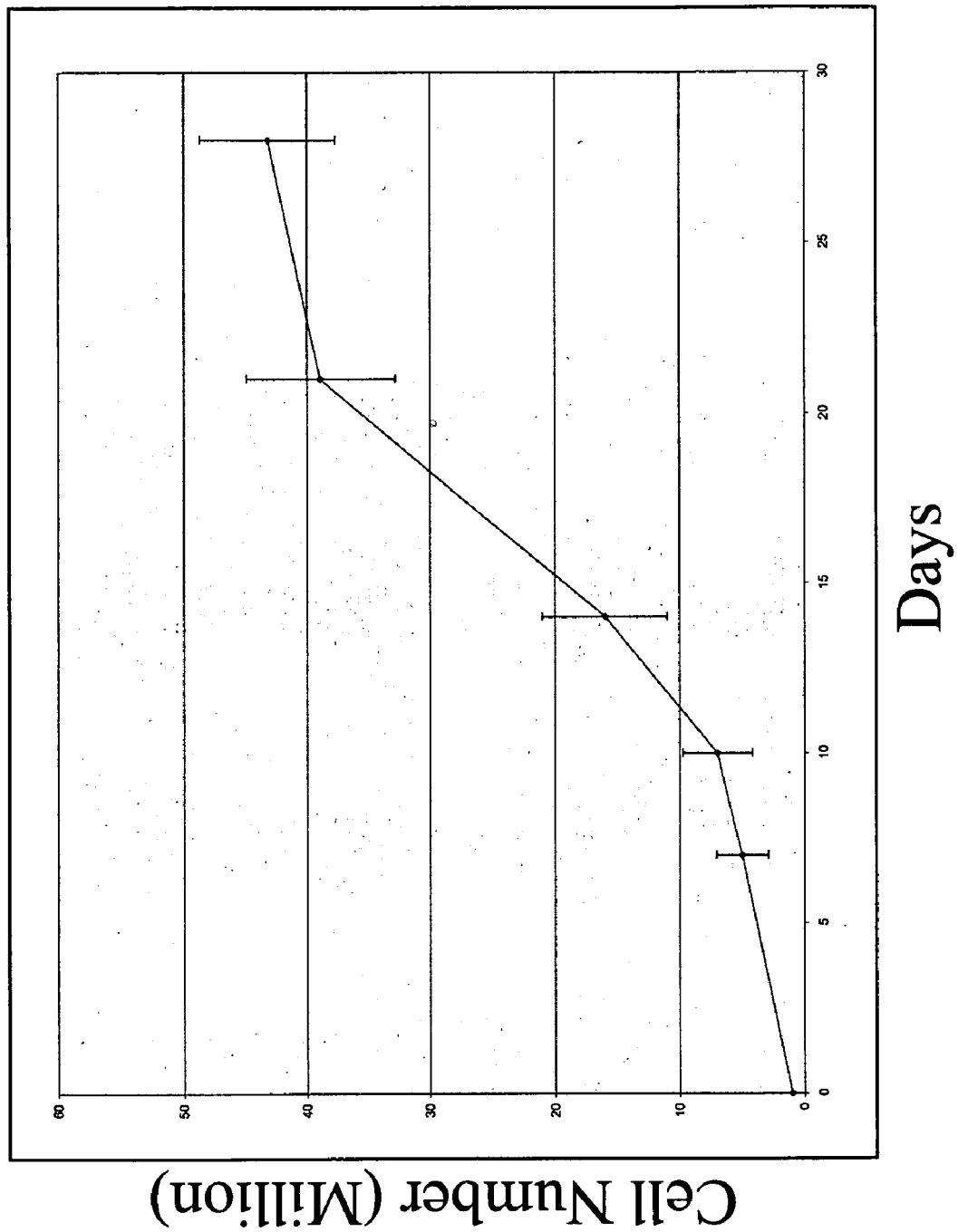
FIG. 1A is a chart showing cell number over time of $10^6$ total bone marrow cells cultured in serum-free medium with SCF, TPO, IGF-2, and FGF-1; total cell numbers were counted at day 7, 10, 14, and 28.

Methods of ex vivo cell culture capable of expanding hematopoietic cells that maintain pluripotency are provided. Also provided are hematopoietic stem cells, methods for identifying hematopoietic stem cells, and kits for propagating or expanding hematopoietic stem cells ex vivo.

Ex Vivo Cultures of Hematopoietic Stem Cells

The present invention provides methods for promoting the expansion of hematopoietic stem cells (HSCs) in culture.

As used herein, expansion includes any increase in cell number. Expansion includes, or example, in an increase in the number of hematopoietic stem cells over the number of HSCs present in the cell population used to initiate the culture.

As used herein, hematopoietic stem cell (HSC) refers to animal, preferably mammalian, more preferably human cells that have the ability to differentiate into any of several types of blood cells, including red blood cells, white blood cells, including lymphoid cells and myeloid cells. HSCs can include hematopoietic cells having long-term engrafting potential in vivo. Long term engrafting potential (e.g., long term hematopoietic stem cells) can be determined using animal models or in vitro models. Animal models for long-term engrafting potential of candidate human hematopoietic stem cell populations include the SCID-hu bone model (Kyoizumi et al. (1992) Blood 79:1704; Murray et al. (1995) Blood 85(2) 368-378) and the in utero sheep model (Zanjani et al. (1992) J. Clin. Invest. 89:1179). For a review of animal models of human hematopoiesis, see Srour et al. (1992) J. Hematother. 1:143-153 and the references cited therein. An in vitro model for stem cells is the long-term culture-initiating cell (LTCIC) assay, based on a limiting dilution analysis of the number of clonogenic cells produced in a stromal co-culture after 5-8 weeks (Sutherland et al. (1990) Proc. Nat'l Acad. Sci. 87:3584-3588). The LTCIC assay has been shown to correlate with another commonly used stem cell assay, the cobblestone area forming cell (CAFC) assay, and with long-term engrafting potential in vivo (Breems et al. (1994) Leukemia 8:1095).

Methods for expanding hematopoietic stem cells ex vivo comprise culturing a population of cells in a medium containing an effective amount of insulin-like growth factor (IGF) and at least one of fibroblast growth factor (FGF), thrombopoietin (TPO), or stem cell factor (SCF), under conditions sufficient for expansion of hematopoietic stem cells. An "effective amount" is an amount sufficient to effect beneficial or desired results. An effective amount can be administered in one or more administrations. An effective amount of the cytokines or factors used herein can be an amount that is sufficient to promote expansion of hematopoietic stem cells ex vivo.

In one aspect the medium formulations for expansion of HSCs are supplemented with fibroblast growth factor (FGF) (e.g., FGF-1 or FGF-2), insulin-like growth factor (e.g., IGF-2, or IGF-1) thrombopoietin (TPO), and stem cell factor (SCF). The concentrations of the factors can range from about 0.1 ng/mL to about 500 ng/mL, preferably from about 1 ng/mL to about 100 ng/mL, most preferably from about 10 ng/ml to 50 ng/ml. In one embodiment the cytokines are FGF-1, TPO, IGF-2, and SCF. In one embodiment SCF is present at 10 ng/ml is present, TPO is present at 20 ng/ml, IGF-2 is present at 20 ng/ml and FGF-1 is present at 10 ng/ml. Other cytokines may be added, alone or in combination, and include but are not limited to G-CSF, GM-CSF, IL-1α, and IL-11.

The population of cells used in the cell culture may be derived from any tissue source expected to contain HSCs, including bone marrow, both adult and fetal, cytokine mobilized or chemotherapy mobilized peripheral blood, fetal liver, embryonic yolk sac, fetal spleen, or umbilical cord blood. The use of umbilical cord blood is discussed, for instance, in Issaragrishi et al. (1995) N. Engl. J. Med. 332:367-369. Bone marrow cells can be obtained from a source of bone marrow, including but not limited to, ilium (e.g., from the hip bone via the iliac crest), tibia, femora, vertebrate, or other bone cavities. For isolation of bone marrow, an appropriate solution can be used to flush the bone, including, but not limited to, salt solution, conveniently supplemented with fetal calf serum (FCS) or other naturally occurring factors, in conjunction with an acceptable buffer at low concentration, generally from about 5-25 mM. Convenient buffers include, but are not limited to, HEPES, phosphate buffers and lactate buffers. Bone marrow can also be aspirated from the bone in accordance with conventional techniques. Preferably, the population of cells are human cells, but can be derived from any suitable animal, e.g., human, simian, porcine or murine.

The cell population used in cell culture can be subjected to methods of enrichment for hematopoeitic stem cells. Means for isolating sub-populations of cells enriched for hematopoeitic stem cells are known to those skilled in the art. As described below, the population of cells can be substantially enriched in hematopoietic stem cells and substantially free of stromal cells. "Substantially free of stromal cells" includes a cell population which, when placed in a culture system as described herein, does not form an adherent cell layer. Populations highly enriched in stem cells and methods for obtaining them are described in PCT/US94/09760; PCT/US94/08574 and PCT/US94/10501.

For example, a purified "side population" (SP) cells obtained from bone marrow or other sources can be used. Methods for isolating enriched populations of HSCs are known to those in the art, e.g., methods for obtaining SP cells are described in Goodell et al. J Exp Med 183, 1797-806 (Apr. 1, 1996).

Separation of stem cells from a cell population can be performed by any number of methods, including cell sorters, magnetic beads, and packed columns. Exemplary of a highly enriched stem cell population is a population having the $CD34^+Thy-1^+LIN^-$ phenotype as described in U.S. Pat. No. 5,061,620. It will be appreciated by those of skill in the art that the enrichment provided in any stem cell population will be dependent both on the selection criteria used as well as the purity achieved by the given selection techniques. Methods for isolating highly enriched populations of hematopoeitic stem cells are further provided in U.S. Pat. No. 5,681,559.

In another embodiment, the cell population is initially subject to negative selection techniques to remove those cells that express lineage specific markers and retain those cells which are lineage negative ("$Lin^-$"). $Lin^-$ cells generally refer to cells which lack markers associated with differentiated blood cells such as T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils. Methods of negative selection are known in the art.

For example, the absence or low expression of markers or surface markers such as lineage specific markers can be identified by the lack of binding of antibodies specific to the marker. In one embodiment, lineage specific markers include, but are not limited to, at least one of CD2, CD14, CD15, CD16, CD19, CD20, CD38, HLA-DR and CD71; more preferably, at least one of CD14, CD15 and CD19. As used herein, "$Lin^-$" refers to cells that lack expression or surface expression of at least one lineage specific marker. Suitable lineage specific markers for human and mouse are well know in the art. Suitable Lin markers for human include CD2, CD3, CD14, CD16, CD19, CD24, CD56, CD66b, Glycophorin A. Suitable Lin markers for mouse include CD5, B220, Mac-1, Gr-1, Ter119. A cocktail of antibodies that recognize one or more the Lin markers can be used to select cells that lack expression of lineage specific markers.

Various techniques can be used to separate or isolate the cells based on expression or surface expression of markers such as lineage markers. For example, antibodies such as monoclonal antibodies can be used to identify markers associated with particular cell lineages and/or stages of differentiation. The antibodies can be attached to a solid support to such that cells that express the markers are immobilized, thereby allowing the separation of cells that express that marker from cells that do not express the marker. The separation techniques used should maximize the retention of viable cells to be collected. Such separation techniques can result in sub-populations of cells where up to 10%, usually not more than about 5%, preferably not more than about 1%, of the selected cells do not express the marker in question. The particular technique employed will depend upon efficiency of separation, associated cytotoxicity, ease and speed of performance, and necessity for sophisticated equipment and/or technical skill. An "isolated" or "purified" population of cells is substantially free of cells and materials with which it is associated in nature, in particular, free of cells that lack the desired phenotype. Substantially free or substantially purified includes at least 50% hematopoietic stem cells, preferably at least 70%, more preferably at least 80%, and even more preferably at least 90% hematopoietic stem cells.

Procedures for separating the population of cells or isolating a sub-population of cells can include, but are not limited to, physical separation, magnetic separation, antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of physical separation techniques also include those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

Techniques providing accurate separation of cells further include flow cytometry, which can have varying degrees of sophistication, e.g., a plurality of color channels, low angle and obtuse light scattering detecting channels, impedance channels, etc. Cells also can be selected by flow cytometry based on light scatter characteristics, where stem cells are selected based on low side scatter and low to medium forward scatter profiles. Cytospin preparations show for example, that enriched stem cells to have a size between mature lymphoid cells and mature granulocytes.

For example, in a first separation step, anti-CD34 can be labeled with a first fluorochrome, while the antibodies for the various dedicated lineages, can be conjugated to a fluorochrome with different and distinguishable spectral characteristics from the first fluorochrome. While each of the lineages can be separated (e.g., removed from the cell population) in more than one "separation" step, the lineages can be separated at the same time and/or at the same time with positive selection. The cells can be separated from dead cells, by using dyes that label dead cells (including but not limited to, propidium iodide (PI)). Separation based on negative markers, positive markers, viability and the like can be conducted separately in any order or simultaneously.

The cells described above can be used immediately or frozen at liquid nitrogen temperatures and stored for long periods of time, being thawed and capable of being reused. Once thawed, the cells can be expanded by use of the methods described herein.

In the method of expanding hematopoietic stem cells ex vivo, culturing includes any method suitable for propagating cells in vitro or ex vivo. It is understood that the descendants of the cells used to initially innoculate the culture may not be completely identical (either morphologically, genetically, or phenotypically) to the parent cell. In one embodiment, the population of cells is incubated in a suitable medium at a suitable temperature and atmosphere. The medium can be supplemented with a variety of different nutrients, heparin, antibiotics, growth factors, cytokines, and the like. In most aspects, suitable conditions comprise culturing at about 33° C. to about 39° C., and preferably at about 37° C. In one embodiment the oxygen concentration is about 4 to about 20%. The medium can be replaced throughout the culture period. In one preferred embodiment, half of the medium is replaced twice per week with fresh media.

The population of cells is placed in a suitable container for expanding the HSCs. For example, suitable containers for culturing the population of cells include flasks, tubes, or plates. In one embodiment, the flask can be T-flask such as a 12.5 cm², or a 75 cm² T-flask. The plate can be a 10 cm plate, a 3.5 cm plate or a multi-welled plate such as a 12, 24, or 96 well plate. The wells can be flat, v-bottom or u-bottom wells. The containers can be treated with any suitable treatment for tissue culture to promote cell adhesion or to inhibit cell adhesion to the surface of the container. Such containers are commercially available from Falcon, Corning or Costar. As used herein, "expansion container" also is intended to include any chamber or container for expanding cells whether or not free standing or incorporated into an expansion apparatus.

Preferably, the cell density of the cultured population of cells such as total bone marrow is from at least about $1\times10^2$ cells to about $1\times10^7$ cells/mL, and even more preferably from about $1\times10^5$ to about $1\times10^6$ cells/mL, and cells are cultured at an oxygen concentration of from about 2 to 20%. In one embodiment, SP bone marrow cells are cultured a lower density, for example from about $1\times10^2$ to $5\times10^3$ cells/ml. In a separate aspect, the inoculation population of cells is derived from mobilized peripheral blood and is from about 20,000 cells/mL to about 50,000 cells/mL, preferably 50,000 cells/mL.

Various media can be used to culture the population of cells such that HSCs are expanded. Such media include, but are not limited to Dulbecco's MEM, IMDM, X-Vivo 15 (serum-depleted) and RPMI-1640. Preferably the medium is serum free. In one preferred embodiment, the medium is serum free StemSpan (Stem Cell Technologies) supplemented with 10 ug/ml heparin.

The cells are cultured for a suitable time, sufficient to expand the number of HSCs. The cells can be cultured, for example, for at least one week, or about 10 days, or at least about 2 weeks. In one embodiment, the cells are cultured for 7 days to 14 days. The cells can also be cultured for longer periods of time. For example, the cells can be cultured for at least about four weeks.

The method for expanding hematopoietic stem cells can further comprise selecting or isolating cells that express at least one positive cell surface marker. As used herein, a marker is expressed by a cell or on the surface of a cell if the marker can be detected using standard methods in the art for detecting cell surface markers. A marker is not expressed by a cell or on the surface of a cell if is not detectable using standard methods in the art for detecting cell surface markers. Methods for determining whether a marker is expressed on the surface of the cell are well known in the art. For example, methods described herein for separating the population of cells into sub-population based on the presence or absence of one or more markers maybe used. Positive surface markers include, for example, Sca-1, IGF-2 receptor, CD31, or Kit. In another embodiment, the method for expanding hematopoietic cells can further comprise selecting or isolating cells that do not express at least one negative cell surface marker. Negative surface markers include, for example, PrP, Lin, or CD62L. Cells can be selected that express any combination of positive surface markers and that do not express any combination of negative surface markers. For example, cells can be selected that express at least two positive cell surface markers and that do not express at least two negative cell surface markers. In another embodiment, the cells express at least three positive cell surface markers and do not express at least three negative cell surface markers. In a more particular embodiment, cells can be selected that express Sca-1, IGF-2 receptor, CD31 and Kit and do not express PrP, Lin, and CD62L. In another embodiment, cells can be selected that express Sca-1 and IGF-2 receptor and do not express PrP, Lin, and CD62L. The cells can be selected according to the above criteria either before or after culturing the population of cells.

As used herein, cytokine or factor can include numerous factors that exert a variety of effects on cells, for example, inducing growth or proliferation. Non-limiting examples of additional cytokines which may be used in combination in the practice of the present invention include, interleukin-2 (IL-2), interleukin 3 (IL-3), interleukin 6 (IL-6) including soluble IL-6 receptor, interleukin 12 (IL12), G-CSF, granulocyte-macrophage colony stimulating factor (GM-CSF), interleukin 1 alpha (IL-1 α), interleukin 11 (IL-11), MIP-1 α, leukemia inhibitory factor (LIF), c-kit ligand, and flt3 ligand. The present invention also includes culture conditions in which one or more cytokine is specifically excluded from the medium. Cytokines are commercially available from several vendors such as, for example, Amgen (Thousand Oaks, Calif.), R & D Systems and Immunex (Seattle, Wash.). Cytokine or factor also includes fibroblast growth factor (FGF) (e.g., FGF-1 or FGF-2), insulin-like growth factor (e.g., IGF-2, or IGF-1), thrombopoietin (TPO), and stem cell factor (SCF), or analogs and equivalents thereof. Equivalents thereof include molecules having similar biological activity to these factors (e.g., FGF, TPO, IGF, and SCF) in wild-type or purified form (e.g., recombinantly produced). Analogs include fragments retaining the desired activity and related molecules. For example, TPO is a ligand of the mp1 receptor, thus molecules capable of binding the mp1 receptor and initiating one or more biological actions associated with TPO binding to mp1 are also within the scope of the invention. An example of a TPO mimetic is found in Cwirla et. al. (1997) Science 276:1696.

Hematopoietic Stem Cells

The present invention also includes hematopoietic stem cells. The hematopoietic stem cells of the present invention can be produced by the method of the present invention. In one embodiment, the hematopoietic stem cells of the present invention have a surface phenotype of Sca-1$^+$, IFG-2 receptor$^+$, Kit$^+$, CD31$^+$ and one or more of the group consisting of PrP$^-$, Tie-2$^-$, CD62L$^-$, prominin-1$^-$, CD34$^-$, CD38$^-$, and Lin$^-$. In another embodiment, the hematopoietic stem cells of the present invention have a surface phenotype of Sca-1$^+$, IFG-2 receptor$^+$, Kit$^+$, CD31$^+$ and two or more of the group consisting of PrP$^-$, Tie-2$^-$, CD62L$^-$, prominin-1$^-$, CD34$^-$, CD38$^-$, and Lin$^-$. In a preferred embodiment, the hematopoietic stem cells of have a surface phenotype of Sca-1+, IFG-2 receptor+, Kit+, CD31+, PrP−, and Tie-2−.

The HSCs of the present invention can be used for transplantation such as bone marrow transplantation in a subject or host. In one embodiment the HSCs are human long-term bone marrow cultures. Human autologous and allogeneic bone marrow transplantation are currently used as therapies for diseases such as leukemia, lymphoma, and the like. For these procedures, however, a large amount of donor bone marrow must be removed to ensure that there are enough cells for engraftment. The methods of the present invention circumvent this problem because the HSCs are expanded ex vivo. Methods of transplantation are known to those skilled in the art.

The HSCs of the present invention are particularly suited for reconstituting hematopoietic cells in a subject or for providing cell populations enriched in desired hematopoietic cell types. The HSCs of the present invention can be used for reconstituting the full range of hematopoietic cells in an immunocompromised subject following therapies such as, but not limited to, radiation treatment and chemotherapy. Such therapies destroy hematopoietic cells either intentionally or as a side-effect of bone marrow transplantation or the treatment of lymphomas, leukemias and other neoplastic conditions, e.g., breast cancer.

Expanded hematopoietic cells are also useful as a source of cells for specific hematopoietic lineages. The maturation, proliferation and differentiation of hematopoietic stem cells into one or more selected lineages may be effected through culturing the cells with appropriate factors including, but not limited to, erythropoietin (EPO), colony stimulating factors, e.g., GM-CSF, G-CSF, or M-CSF, SCF, interleukins, e.g., IL-1, -2, -3, -4, -5, -6, -7, -8, -13, etc., or with stromal cells or other cells which secrete factors responsible for stem cell regeneration, commitment, and differentiation.

The HSCs of the invention are useful for identifying culture conditions or biological modifiers such as growth factors which promote or inhibit such biological responses of stem cells as self-regeneration, proliferation, commitment, differentiation, and maturation. In this way one may also identify, for example, receptors for these biological modifiers, agents which interfere with the interaction of a biological modifier and its receptor, and polypeptides, antisense polynucleotides, small molecules, or environmental stimuli affecting gene transcription or translation. For example, the present invention makes it possible to prepare relatively large numbers of hematopoietic stem cells for use in assays for the differentiation of stem cells into various hematopoietic lineages. These assays may be readily adapted in order to identify substances such as growth factors which, for example, promote or inhibit stem cell self-regeneration, commitment, or differentiation.

The HSCs of the present invention may also be used to identify and clone genes whose expression is associated with proliferation, commitment, differentiation, and maturation of stem cells or other hematopoietic cells, e.g., by subtractive hybridization or by expression cloning using monoclonal antibodies specific for target antigens associated with these biological events or characteristic of a hematopoietic cell type.

As described below, hematopoeitc stem cells are also important targets for gene therapy in a subject. Expression vectors may be introduced into and expressed in autologous or allogeneic HSCs of the present invention, or the genome of cells may be modified by homologous or non-homologous recombination by methods known in the art. In this way, one may correct genetic defects in an individual or provide genetic capabilities naturally lacking in stem cells. For example, diseases including, but not limited to, β-thalassemia, sickle cell anemia, adenosine deaminase deficiency, recombinase deficiency, and recombinase regulatory gene deficiency may be corrected in this fashion. Diseases not associated with hematopoietic cells can also be treated, e.g., diseases related to the lack of secreted proteins including, but not limited to hormones, enzymes, and growth factors. Inducible expression of a gene of interest under the control of an appropriate regulatory initiation region will allow production (and secretion) of the protein in a fashion similar to that in the cell which normally produces the protein in nature.

Similarly, one may express in expanded hematopoeitc cells a ribozyme, antisense RNA or protein to inhibit the expression or activity of a particular gene product. Drug resistance genes including, but not limited to, the multiple drug resistance (MDR) gene, may also be introduced into cells, e.g., to enable them to survive drug therapy. For hematotrophic pathogens, such as HIV or HTLV-I, and HTLV II, the cells can be genetically modified to produce an antisense RNA, ribozyme, or protein which would prevent the proliferation of a pathogen in hematopoeitc stem cells or differentiated cells arising from the stem cells. One may also disable or modulate the expression of a particular genetic sequence by methods known in the art, including, but not limited to, directly substituting, deleting, or adding DNA by homologous recombination or indirectly by antisense sequences.

In one embodiment, the hematopoietic cells of the invention are genetically modified. Genetic modification can include any addition, deletion or disruption to a cell's normal nucleic acids. The methods of this invention include methods of gene transfer into hematopoietic stem cells, including but not limited to viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters, etc. In one embodiment, a viral vector is used. To enhance delivery of non viral vectors to a cell, the nucleic acid or proteins can be conjugated to antibodies or binding fragments thereof which bind cell surface antigens, e.g., TCR, CD3 or CD4. Liposomes that also comprise a targeting antibody or fragment thereof can be used in the methods of this invention.

As used herein, the terms "transgene" includes genomic DNA, cDNA, synthetic DNA and RNA, mRNA, small interfering RNA, and antisense DNA and RNA which is introduced into the hematopoietic stem cell. The transgene may be heterologous or an additional copy or copies of genetic material normally found in the individual or animal. When cells are to be used as a component of a pharmaceutical composition in a method for treating human diseases, conditions or disorders, the transgene may encode proteins such as therapeutic proteins used to treat the individual and/or to make the cells more amenable to transplantation.

A "viral vector" is defined as a recombinantly produced virus or viral particle that comprises a polynucleotide to be delivered into a host cell, either in vivo, ex vivo or in vitro. Examples of viral vectors include retroviral vectors such as lentiviral vectors; adenovirus vectors; adeno-associated virus vectors and the like. In aspects where gene transfer is mediated by a retroviral vector, a vector construct refers to the polynucleotide comprising the retroviral genome or part thereof, and a therapeutic gene.

Transgenes can be a inserted into vector using methods well known in the art. For example, the transgene (or insert) and vector can be contacted, under suitable conditions, with a restriction enzyme to create complementary ends on each molecule that can pair with each other and be joined together with a ligase. Alternatively, synthetic nucleic acid linkers can be ligated to the termini of an insert. These synthetic linkers contain nucleic acid sequences that correspond to a particular restriction site in the vector. Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art.

Modification of hematopoietic stem cells can comprise the use of an expression cassette created for either constitutive or inducible expression of the introduced transgene. Such an expression cassette can include regulatory elements such as a promoter, an initiation codon, a stop codon, and a polyadenylation signal. The elements are preferably operable in the stem cells or in cells that arise from the stem cells after infusion into an individual. Moreover, the elements can be operably linked to the transgene such that the transgene is operational (e.g., is expressed) in the stem cells. In one embodiment, the transgene encodes a protein and is expressed in the host cell.

A variety of promoters can be used for expression of the transgene. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter. For example, one can use a tissue specific promoter, i.e. a promoter that functions in some tissues but not in others. Such promoters include EF2 responsive promoters, etc. Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells.

Regulatable promoters can also be used. Such regulatable promoters include those using the lac repressor from *E. coli* as a transcription modulator to regulate transcription from lac operator-bearing mammalian cell promoters [Brown, M. et al., *Cell*, 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)]. Other systems include FK506 dimer, VP16 or p65 using astradiol, RU486, diphenol murislerone or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell*, 49:603-612 (1987)]; Gossen and Bujard (1992); [M. Gossen et al., *Natl. Acad. Sci. USA*, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycling inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter [F. Yao et al., *Human Gene Therapy*, supra]. One particular advantage of this tetracycline inducible switch is that it does not require the use of a tetracycline repressor-mammalian cells transactivator or repressor fusion protein, which in some instances can be toxic to cells [M. Gossen et al., *Natl. Acad. Sci. USA*, 89:5547-5551 (1992); P. Shockett et al., *Proc. Natl. Acad. Sci. USA*, 92:6522-6526 (1995)], to achieve its regulatable effects.

The effectiveness of some inducible promoters can be increased over time. In such cases one can enhance the effectiveness of such systems by inserting multiple repressors in tandem, e.g., TetR linked to a TetR by an IRES. Alternatively, one can wait at least 3 days before screening for the desired function. While some silencing may occur, it can be minimized by using a suitable number of cells, preferably at least $1 \times 10^4$, more preferably at least $1 \times 10^5$, still more preferably at least $1 \times 10^6$, and even more preferably at least $1 \times 10^7$. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired transgene into the hematopoeitic stem cells of the invention. These marker genes can be under the control of any promoter or an inducible promoter. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

Preferably, the HSC cells are transduced with a therapeutic gene. Preferably the transduction is via a viral vector such as a retroviral vector (as described in for example, in WO 94/29438, WO 97/21824 and WO 97/21825). When transduction is ex vivo, the transduced cells are subsequently administered to the recipient or host animal. Thus, the invention encompasses delivery of transgenes to a host animal and treatment of diseases amenable to gene transfer into HSCs, by administering the gene ex vivo or in vivo by the methods disclosed herein. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance protein.

Diseases other than those associated with hematopoietic cells can also be treated by genetic modification, where the disease is related to the lack of a particular secreted product including, but not limited to, hormones, enzymes, interferons, growth factors, or the like. By using an appropriate regulatory sequence, inducible production of the deficient protein can be achieved, even though production will be in a different cell type from the cell type that normally produces such protein. It is also possible to insert a ribozyme, antisense or other message to inhibit particular gene products or susceptibility to diseases, particularly hematolymphotropic diseases.

A therapeutic gene can be an entire gene or only the functionally active fragment of the gene capable of compensating for the deficiency in the patient that arises from the defective endogenous gene. Therapeutic gene can also encode or encompasses antisense oligonucleotides, small interfering RNA, genes useful for antisense suppression and ribozymes for ribozyme-mediated therapy and the like. Generally, gene therapy will involve the transfer of a single therapeutic gene although more than one gene may be necessary for the treatment of particular diseases. In one embodiment, the therapeutic gene is a normal, e.g. wild-type, copy of the defective gene or a functional homolog. In a separate embodiment, the therapeutic gene is a dominant inhibiting mutant of the wild-type. More than one gene can be administered per vector or alternatively, more than one gene can be delivered using several compatible vectors. Depending on the genetic defect, the therapeutic gene can include the regulatory and untranslated sequences. For gene therapy in human patients, the therapeutic gene will generally be of human origin although genes from other closely related species that exhibit high homology and biologically identical or equivalent function in humans may be used, if the gene product does not induce an adverse immune reaction in the recipient. For example, a primate insulin gene whose gene product is capable of converting glucose to glycogen in humans would be considered a functional equivalent of the human gene. The therapeutic gene suitable for use in treatment will vary with the disease. For example, a suitable therapeutic gene for treating sickle cell anemia is a normal copy of the globin gene. A suitable therapeutic gene for treating SCID is the normal ADA gene.

Methods of Identifying Ex Vivo Expanded Hematopoietic Stem Cells

The present invention includes methods for identifying cultured hematopoietic stem cells or HSCs that have been expanded ex vivo. In one embodiment, the identified HSCs retain HSC activity. The method for identifying hematopoietic stem cells comprises characterizing surface phenotype of cultured cells. The cells having the desired phenotype can be identified by any method that can identify surface markers, such as a FACS based isolation method. Suitable methods include methods described herein for separating or isolating a sub-population of cells from the cell population.

In one embodiment, the identified cells retain at least 25% of the pluripotency of the initial HSCs used (e.g., the population of cells prior to culturing), still more preferably at least 50% of the pluripotency, even more preferably at least 75% of the pluripotency. Yet more preferably, the cells identified retain at least 90% of the pluripotency.

In one embodiment, a surface phenotype of Sca-1$^+$, IGF-2 receptor$^+$, Kit$^+$, CD31$^+$ and of one or more of the group consisting of PrP$^-$, Tie-2$^-$, CD62L$^-$, prominin-1$^-$, CD34$^-$, CD38$^-$, and Lin$^-$ is indicative of a hematopoietic stem cell. In another embodiment, a surface phenotype of Sca-1$^+$, IGF-2 receptor$^+$, Kit$^+$, CD31$^+$ and two or more of PrP$^-$, Tie-2$^-$, CD62L$^-$, prominin 1$^-$, CD34$^-$, CD38$^-$, and Lin$^-$ is indicative of a hematopoietic stem cell. In another embodiment, a surface phenotype of Sca-1$^+$, IGF-2 receptor$^+$, Kit$^+$, CD31$^+$ and of three or more of PrP$^-$, Tie-2$^-$, CD62L$^-$, prominin 1$^-$, CD34$^-$, CD38$^-$, and Lin$^-$ is indicative of a hematopoietic stem cell. In still another embodiment, a surface phenotype of Sca-1$^+$, IGF-2 receptor$^+$, Kit$^+$, CD31$^+$, PrP$^-$, Tie-2$^-$, CD62L$^-$, prominin 1$^-$, CD38$^-$, and Lin$^-$ is indicative of a hematopoietic stem cell. As used herein, the + notation indicates that a cell expresses the indicated marker or expresses the indicated marker on the cell surface and the − notation indicates that a cell does not express or does not express on the surface, the indicated marker. Methods for determining whether a cell expresses a given marker are well know in the art and described above.

Kits

As a result of the present invention, it is now possible to prepare kits for readily expanding hematopoietic stem cells ex vivo, according the methods provided herein. Therefore, kits for propagating or expanding hematopoietic stem cells ex vivo are also provided. In one embodiment, the kit comprises at least one factor selected from the group consisting of IGF-2, SCF, TPO, and FGF-1 and instructions for expanding hematopoietic stem cells ex vivo. In another embodiment, the kit comprises comprising two of the factors from group consisting of IGF-2, SCF, TPO, and FGF-1. In another embodiment, the kit comprises each of IGF-2, SCF, TPO, and FGF-1. The factors can be provided in amounts or concentrations that are ready to use in culture or may be provided in higher concentrations to be diluted in a suitable medium for cell culture.

The following example is not intended to limit the present invention in any way.

EXAMPLE

Materials and Methods

Animals

C57 BL/6 CD45.2 and CD45.1 mice were purchased from the Jackson Laboratory or the National Cancer Institute and were maintained at the Whitehead Institute animal facility.

Cell Culture

Total C57 BL/6 CD45.2 bone marrow cells were plated at a density of $10^6$ cells/ml in serum-free medium StemSpan (StemCell Technologies) supplemented with 10 ug/ml heparin (Sigma), 10 ng/ml SCF, 20 ng/ml TPO, 20 ng/ml IGF-2, and 10 ng/ml FGF-1 (R&D Systems). Half of the medium was replaced twice per week with fresh medium, and the total volume for $10^6$ input cells was increased to 1.5 ml and 6 ml at day 4 and day 7, respectively.

Twenty five bone marrow SP cells were cultured in 50 µl of the above medium in one well of a U-bottom 96-well plate (Corning 3799) for 7 days. The cells were then transferred to 0.5 ml of medium in one well of a 24 well plate for 3 days.

Flow Cytometry

Donor bone marrow cells were isolated from 6-10 week old C57BL/6 CD45.2 mice. Lin$^-$ Sca-1$^+$Kit$^+$ cells and SP cells were detected or sorted as described (C. C. Zhang, H. F. Lodish, *Blood* 103, 2513-21 (Apr. 1, 2004)). Anti-Tie-2-PE and anti-prominin-PE were purchased from eBioscience. Polyclonal rabbit anti-Mpl was developed by Dr. Wei Tong in the Lodish laboratory and anti-rabbit-PE was used as secondary antibody. For Endoglin detection, the staining of anti-endoglin5 mAb (BD Pharmingen) followed by anti-rat-PE/CY5.5 was performed before other staining. Anti-PrP mAb (SAF-83, Cayman Chemical, Ann Arbor, Mich.) was FITC-conjugated using the Quick-Tag FITC conjugation kit (Roche) or used as an unconjugated antibody as indicated. All other primary antibodies were from BD Pharmingen. Lin$^-$Sca-1$^+$PrP$^{+/-}$ cells or Lin$^-$Kit$^+$PrP$^{+/-}$ cells were detected or sorted by staining with biotinylated Lin$^+$ antibody cocktail, followed by streptavidin-APC, anti-PrP-FITC, and either anti-Sca-1-PE or anti-Kit-PE. For detecting and isolating Lin$^-$PrP$^-$Sca-1$^+$CD62L$^-$ IGF-2 receptor$^+$ fraction, cells were stained by 2 ug/ml of IGF2-hFc for 30 min, followed by anti-human IgG1-PE, anti-PrP, anti-mouse-PE/CY5.5, a cocktail of biotinylated lineage-specific antibodies, streptavidin-PE/CY5.5, anti-Sca-1-FITC, and anti-CD62L-PE.

After two washes, the cells were detected in a FacsCalibur instrument, or isolated by FACS sorting in a MoFlo® cell sorter.

For reconstitution analysis, peripheral blood cells were collected by retro-orbital bleeding, followed by lysis of red blood cells and staining with anti-CD45.2-FITC, anti-CD45.1-PE, anti-Thy1.2-PE, anti-B220-PE, anti-Mac-1-PE, anti-Gr-1-PE, or anti-Ter119-PE monoclonal antibodies (BD Pharmingen). FACS analyses were performed on a FACS-Calibur® instrument.

Competitive Reconstitution Analysis

The reconstitution protocol was essentially as described previously (C. C. Zhang, and H. F. Lodish 2004)). Briefly, the indicated numbers of CD45.2 donor cells were either directly injected or injected after mixing with $1 \times 10^5$ or $2 \times 10^5$ (as indicated) freshly isolated CD45.1 competitor bone marrow cells, intravenously into a group of 6-9 week old CD45.1 mice irradiated with a total dose of 10 Gy. To measure reconstitution of transplanted mice, peripheral blood was collected by retro-orbital bleeding at the indicated times post-transplant and the presence of CD45.1$^+$ and CD45.2$^+$ cells in lymphoid and myeloid compartments were measured. The calculation of CRUs in limiting dilution experiments was conducted as previously described (C. C. Zhang, H. F. Lodish, *Blood* 103, 2513-21 (Apr. 1, 2004)).

Summary

Ex vivo expansion of hematopoietic stem cells (HSCs) is important for clinical application and stem cell research, and investigation of the surface phenotype of ex vivo expanded HSCs will be critical to their purification and analysis. Provided herein is a simple culture system for expanding bone marrow HSCs. By competitive repopulation analyses, a more than 20-fold increase in numbers of long-term HSCs after 10-day culture of total bone marrow cells was observed. Culture of BM SP cells, a highly-enriched stem cell population, for 10 days resulted in a 14 fold of expansion of repopulating HSCs. Using this culture system and competitive repopulation analyses, the engraftment potential of subpopulations of cultured cells, which were separated based on expression of a group of known in vivo HSC markers or surface proteins was examined. Similar to in vivo HSCs, donor-derived chimerism resulted from transplants of cells that are only positive for Sca-1, Kit, CD31, and bind to a fusion protein of IGF2 and human IgG1 Fc fragment (as detected by IGF2-hFc binding). Surprisingly, as described herein, the phenotype of cultured HSCs is different from freshly isolated HSCs, and the repopulating cultured BM HSCs are contained in the Lin$^-$ Sca-1$^+$Kit$^+$CD31$^+$IGF2-hFc$^+$ PrP$^-$Tie-2$^-$prominin-1$^-$ CD34$^-$CD62L$^-$ CD38$^-$ cell population. Furthermore, a demonstrated herein the Lin$^-$Sca-1$^+$ IGF2-hFc$^+$PrP$^-$CD62L$^-$ phenotype is an efficient and practical marker combination for enriching expanded HSCs. The culture system and the study of the surface phenotype of ex vivo expanded HSCs will be valuable for ex vivo expansion, genetic modification, analysis and purification of HSCs, and the design of new in vitro screening assays for HSC activity.

The antigen phenotype identified on murine HSCs from freshly isolated bone marrow includes Lin$^-$, Sca-1$^+$, Kit$^+$, Mpl$^+$, CD34$^-$, CD38$^+$, Endoglin$^+$, Tie-2$^+$, IGF2 receptor$^+$, and CD31$^+$ (C. C. Zhang, H. F. Lodish 2004, G. J. Spangrude, S. Heimfeld, I. L. Weissman, *Science* 241, 58-62 (Jul. 1, 1988); M. Osawa, K. Hanada, H. Hamada, H. Nakauchi, *Science* 273, 242-5 (Jul. 12, 1996); C. Z. Chen, L. Li, M. Li, H. F. Lodish, *Immunity* 19, 525-33. (2003); F. Arai et al., *Cell* 118, 149-61 (Jul. 23, 2004); G. P. Solar et al., *Blood* 92, 4-10 (Jul. 1, 1998); A. H. Yin et al., *Blood* 90, 5002-12 (Dec. 15, 1997); C. I. Baumann et al., *Blood* 104, 1010-6 (Aug. 15, 2004); and T. Sato, J. H. Layer, M. Ogawa, *Blood* 94, 2548-54 (Oct. 15, 1999)), and Prion protein$^+$ (PrP$^+$).

Results

Total mouse bone marrow cells (FIG. 1) or bone marrow SP cells (FIG. 2) were grown in serum-free medium containing low concentrations of SCF, TPO, IGF-2, and FGF-1. $1 \times 10^6$ total bone marrow cells/ml were seeded. After 10 days of culture, the number of total cells increased 7 fold to $7.2 \pm 2.8 \times 10^6$ (FIG. 1A). The cultured cells contain mostly suspension cells with a minor adherent cell subpopulation.

Figure 1B:
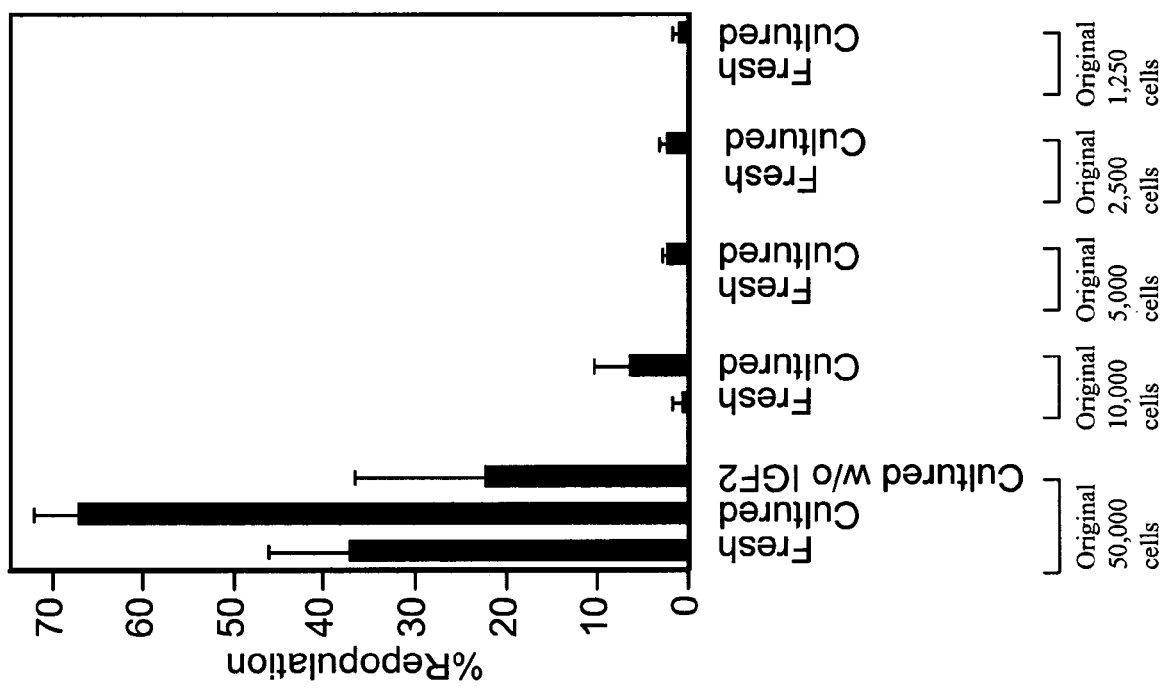
FIG. 1B is a comparison of the long-term repopulation potential of 10 day cultured and freshly isolated bone marrow cells. $5\times10^4$, $1\times10^4$, 5,000, 2500, or 1250 freshly isolated CD45.2 bone marrow cells, as well as $3.5\times10^5$, $7\times10^4$, $3.5\times10^4$, $1.75\times10^4$, or $8.75\times10^3$ of 10 day cultured bone marrow cells (equivalent to 5×10⁴, 1×10⁴, 5,000, 2500, or 1250 initially plated CD45.2 cells respectively) mixed with $10^5$ CD45.1 competitors and transplanted into lethally irradiated recipients (n=6).
Figure 1E:
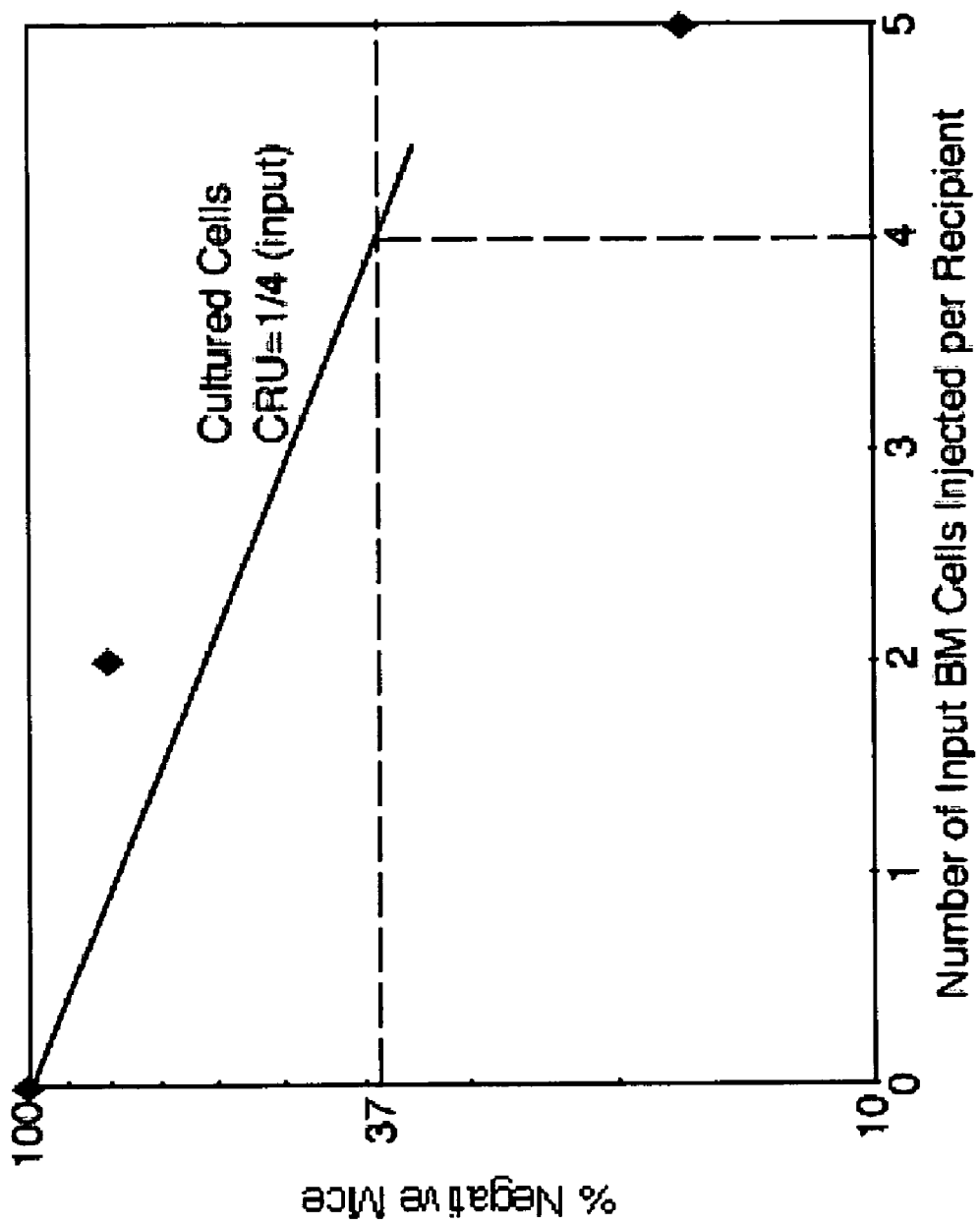
FIG. 1E shows limiting dilution analysis of the repopulating ability of total bone marrow cells before and after in vitro culture.

Competitive repopulation assays were performed to test whether ex vivo expanded cells were capable of engraftment. Various numbers of fresh and cultured CD45.2 cells were mixed with $10^5$ CD45.1 fresh bone marrow competitors and injected into lethally irradiated CD45.1 recipients. A representative result from three independent experiments is shown in FIG. 1B. When $3.5 \times 10^5$ expanded cells (equivalent to $5 \times 10^4$ initially plated CD45.2 cells) were competitively transplanted, an average hematopoietic chimerism of 67.2% was observed 4 months after transplantation. This is much higher than the 37.5% engraftment shown by the equivalent $5 \times 10^4$ uncultured cells. Importantly, this expansion of HSCs was dependent on the presence of IGF-2 in the culture, as the same cultured cells without IGF-2 in the medium had a significantly lower engraftment level of 22.6% (P<0.05, Student's t-test). To avoid donor HSC saturation, fewer cultured cells were also transplanted and compared their engraftment with equivalent numbers of freshly isolated cells. $1 \times 10^4$, 5,000, 2500, or 1250 freshly isolated cells grew to $7 \times 10^4$, $3.5 \times 10^4$, $1.8 \times 10^4$, or 9000 cells respectively. While $1 \times 10^4$, 5,000, 2500, or 1250 freshly isolated BM cells showed an average of 0.6%, 0%, 0%, or 0% engraftment, respectively, their culture progeny repopulated 6.5%, 2.3%, 2.3%, or 1.5% of the recipients, respectively. It is noteworthy that the progeny of 1,250 input cells produced a higher level of engraftment to that resulting from 10,000 input cells, suggesting a dramatic increase of stem cell activity. The progeny of $5 \times 10^4$ cells, after culture, repopulated lymphoid and myeloid lineages 4 months post-transplant, with 68% of the T lineage, 80% of the B lineage, and 56% of the myeloid lineage chimeric at this time (FIG. 1C). BM of the primary transplanted mice was pooled and transplanted into secondary irradiated recipients. These cells repopulated 52% of the T lineage, 65% of the B lineage, and 84% of the myeloid lineage (FIG. 1D). These data indicate a net expansion of LT-HSCs.

The limiting dilution experiment (C. L. Miller, C. J. Eaves, *Proc Natl Acad Sci USA* 94, 13648-53 (Dec. 9, 1997)) in FIG. 1E demonstrates that the cultured bone marrow cells had more than 16-fold increase of LT-HSCs during a 10-day culture. Irradiated CD45.1 congenic mice were injected with $10^5$ CD45.1 bone marrow competitor cells and the indicated numbers of freshly isolated CD45.2 bone marrow cells (■ and solid line) or their progeny after 10 days of culture in serum-free medium with SCF, TPO, IGF-2, and FGF-1 (▽ and dashed line). Plotted is the percentage of recipient mice containing less than 1% CD45.2 lymphoid and myeloid subpopulations in nucleated peripheral blood cells 4 months after transplant versus the number of initial plated cells; note that the abscissa is presented as the number of freshly isolated bone marrow cells. The curve was anchored by the 0 cells/100% negative mice point. The CRU frequency for freshly isolated bone marrow cells is 1 per 34,900 (95% confidence interval for mean: 1/22085 to 1/55177, n=36). That is, as calculated from Poisson statistics, injection, on average, of 34,900 freshly isolated bone marrow cells is sufficient to repopulate 63% (=1-1/e) of transplanted mice. After culture in serum-free medium containing SCF, TPO, IGF-2, and FGF-1, the number of total cells was increased 7-fold, and the number of functional LT-HSCs had increased about 20-fold (P<0.005, Student's t test), as evidenced by the fact that 63% of the mice transplanted with 11,480 cultured cells (or the progeny of, on average, only 1,640 initial bone marrow cells) displayed chimerism. In other words, the CRU frequency was 1 per 1,640 input equivalent bone marrow cells (95% confidence interval for mean: 1/502 to 1/5353, n=36).

In addition to competitive repopulation assays, a graft of only cultured cells, without competitors, was tested for full radioprotection capability (Table 1). A group of lethally irradiated recipients were transplanted with equivalent doses of fresh and cultured bone marrow cells and compared their radioprotection ability. While $10^4$ freshly isolated bone marrow cells failed to rescue all three recipients, their progeny, after culture, rescued 1 out of 3 recipients. For $3 \times 10^4$ input cells, 1 out of 3 recipients were rescued, while their cultured progeny rescued all 3 mice, which is a reconstitution ability normally found in $10^5$ freshly isolated bone marrow cells (Table 1). The fact that the progeny of $3 \times 10^4$ fresh bone marrow could, after culture, provide the radioprotection typically provided by $10^5$ fresh bone marrow cells demonstrates that a significant expansion of HSCs and progenitors can be achieved by this culture system.

Figure 2A:
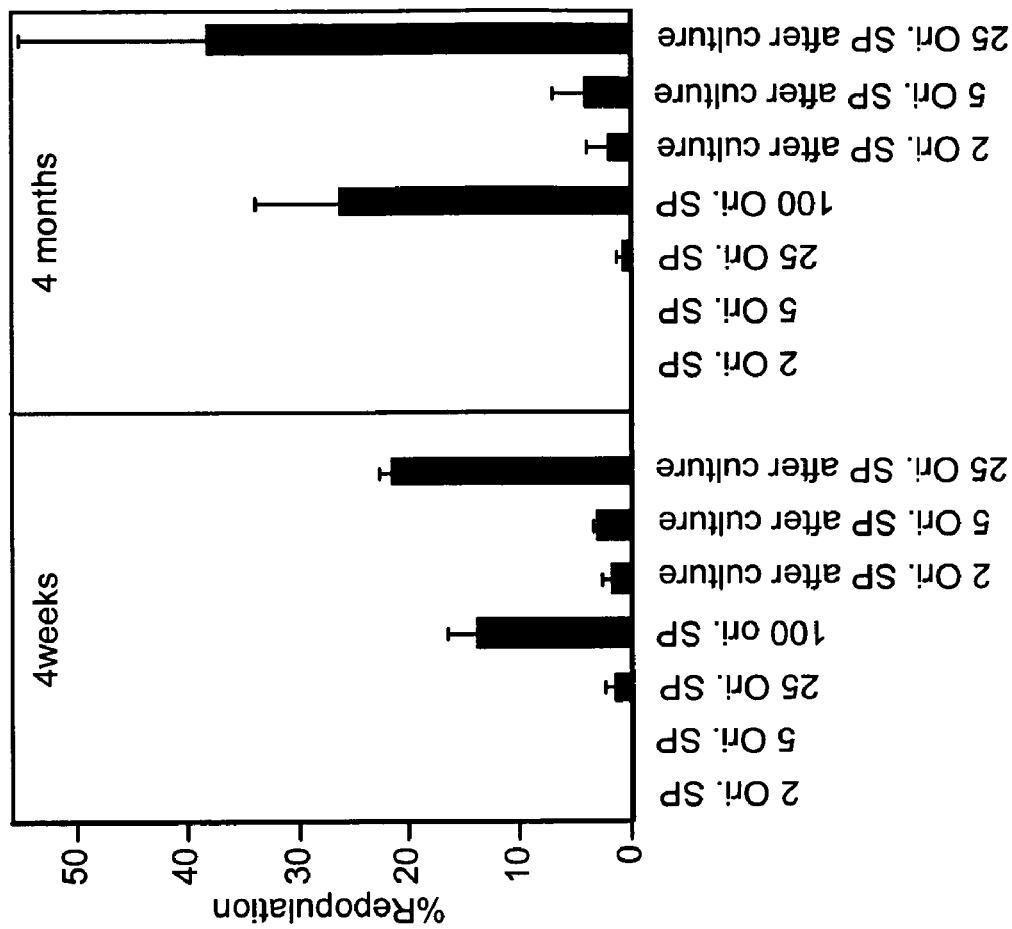
FIG. 2A is a chart showing % repopulation 4 weeks and 4 months after transplant with the indicated cells.
Figure 2C:
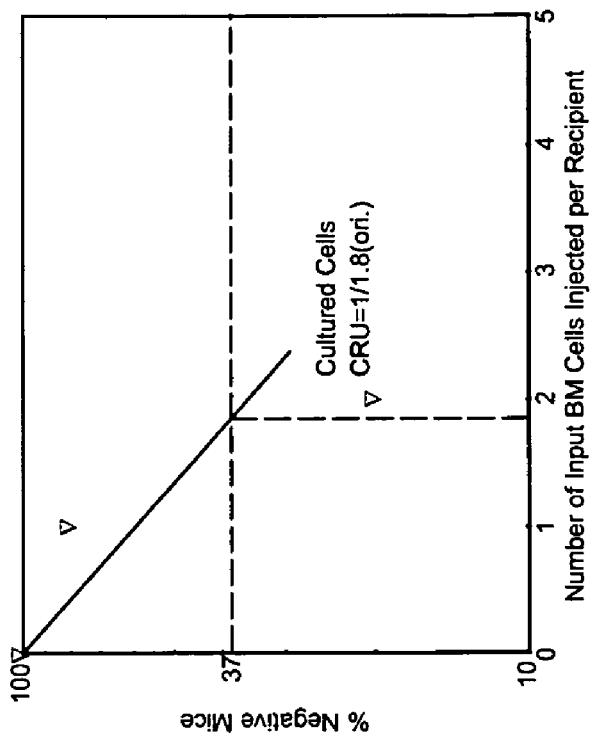
FIG. 2C is a limiting dilution analysis of the repopulating ability of cells after in vitro culture.
Figure 2B:
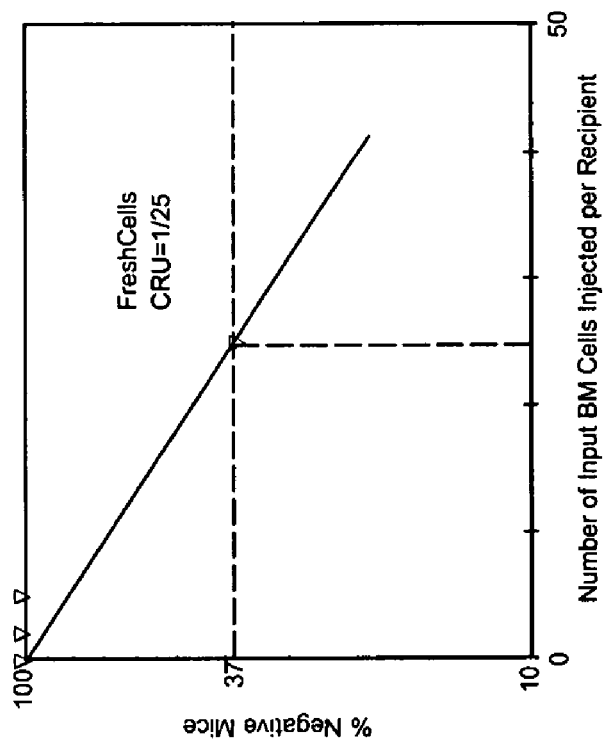
FIG. 2B is a limiting dilution analysis of the repopulating ability of cells before in vitro culture.

To test if the four cytokines can support expansion of highly enriched HSCs, "side population" (SP) cells were purified from adult mouse bone marrow and cultured them in the previously described medium. FIGS. 2A-2C show that the culture dramatically increases in vivo repopulating stem cell activity of bone marrow SP cells. 2, 5, 25 or 100 freshly isolated adult CD45.2 bone marrow SP cells were transplanted directly (with $1 \times 10^5$ CD45.1 competitor bone marrow cells per mouse, n=5-8) into CD45.1 congenic mice. From the same isolation 25 SP cells were cultured 10 days in serum-free medium supplemented with SCF, TPO, IGF-2, and FGF-1. Progenies of the cultured cells equivalent to 2, 5, or 25 input SP cells were coinjected into CD45.1 recipients with $1 \times 10^5$ competitor CD45.1 bone marrow cells (n=5). Peripheral blood cells from transplanted mice were analyzed for the presence of CD45.2$^+$ cells in lymphoid and myeloid compartments at 4 months after transplant.

1 or 5 freshly isolated SP cells were incapable of repopulation. 25 freshly isolated SP cells showed a small repopulation activity, with an average of 0.6% engraftment 4 months post-transplant (FIG. 2A). 100 freshly isolated SP cells showed a 26.2% repopulation. In contrast, the progeny of 1 or 5 plated SP cells cultured for 10 days had an average of 1.5% or 3.4% of engraftment at 4 month post-transplant respectively, which is higher than the average activity of 25 fresh SP cells (FIG. 2A). Similarly, 25 plated SP cells cultured for 10 days had an average of 38.2% repopulation, higher than the average activity of 100 fresh SP cells (FIG. 2A). Based on limiting dilution experiments (FIG. 2B), the CRU of freshly isolated BM SP cells is 1/25 cells (95% confidence interval for mean: 1/14 to 1/44, n=26), and the CRU in cultured SP cells is 1/1.8 of equivalent cells (FIG. 2C, 95% confidence interval for mean: 1/1.3 to 1/2.7, n=20). Therefore, the actual HSC number increased at least 14-fold. Because this fold of expansion of HSCs is similar to cultured total BM cells (FIG. 1E), this combination of cytokines acts directly on HSCs and it is not dependent on potentiation by other cell populations.

Figure 3A:
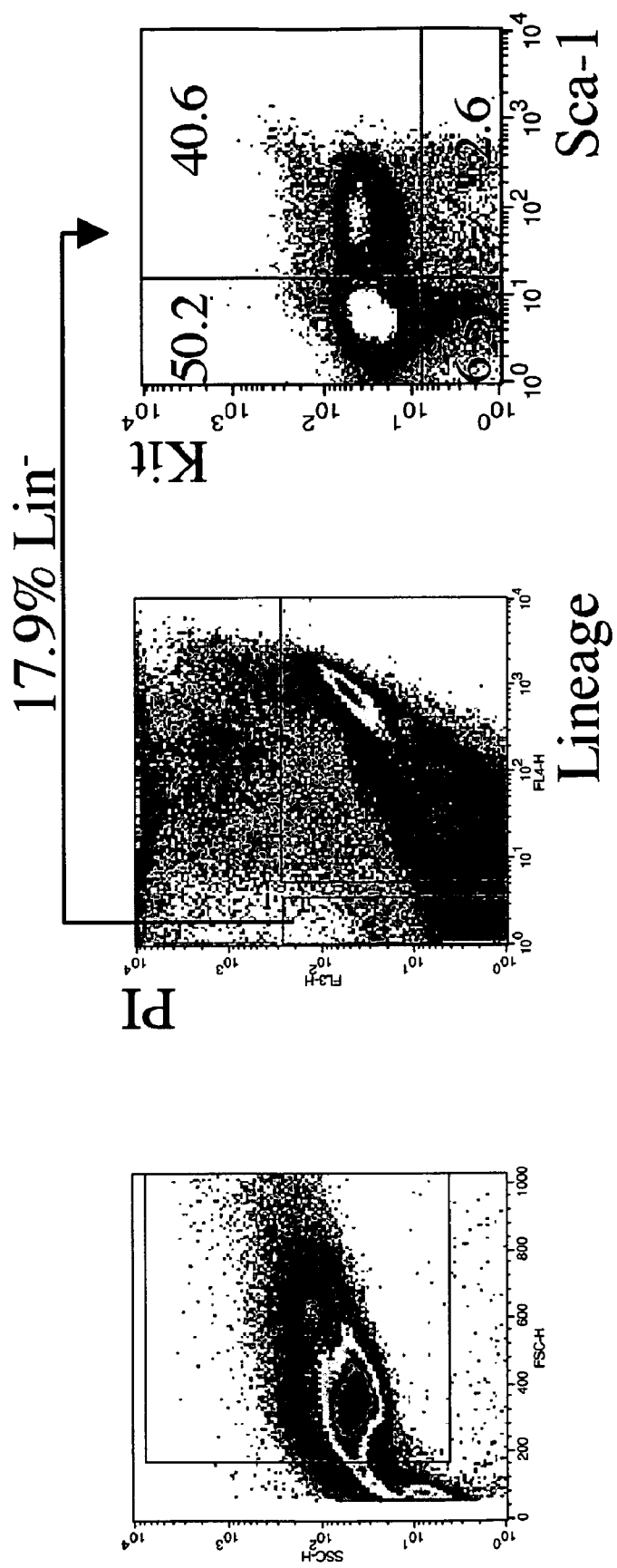
FIG. 3A is a FACS analysis of bone marrow cells cultured for 10 days and stained for Lin, Kit, and Sca-1.

The status of in vivo HSC markers Sca-1 and Kit in cultured bone marrow HSCs was tested. 10 day cultured bone marrow cells in the condition as shown in FIG. 1 were stained with a cocktail of biotinylated lineage-specific antibodies, followed by streptavidin-APC, anti-Sca-1-FITC and anti-Kit-PE. The Lin$^-$ (negative APC-stained) and PI$^-$ cells were gated to show the surface expression of Sca-1/Kit. FIG. 3A shows that after 10 days of culture, 17.9% of total cells are Lin$^-$. Kit$^+$Sca-1$^+$, Kit$^+$Sca-1$^-$, Kit$^-$Sca-1$^+$, Kit$^-$Sca-1$^-$ were 40.6%, 50.2%, 2.6%, and 6.5% of Lin$^-$ cells respectively. Lin$^-$Sca-1$^+$Kit$^+$, Lin$^-$Sca-1$^+$Kit$^-$, Lin$^-$Sca-1$^-$Kit$^+$, and Lin$^-$Sca-1$^-$Kit$^-$ cells were sorted, and their LT-HSC activity was measured by competitive repopulation. After 10 days of culture, 15,000 sorted CD45.2 Sca-1$^+$Kit$^+$, Sca-1$^+$Kit$^-$, Sca-1$^-$Kit$^+$, or Sca-1$^-$Kit cells were transplanted together with $10^5$ CD45.1 competitor cells into lethally irradiated CD45.1 mice (n=4). Peripheral blood cells were analyzed for the presence of CD45.2$^+$ cells in lymphoid and myeloid compartments at 3 weeks and 4 months after transplant. While Lin$^-$Sca-1$^+$Kit$^+$ cells contain both ST- and LT-HSC activities, all of the other three fractions only contained minor ST-HSC activities and no LT-HSC activities (FIG. 3B). This indicates that, similar to in vivo HSCs, LT-HSC activity of cultured HSCs retained in Kit$^+$Sca-1$^+$ fraction.

The HSC activity of cells expressing the in vivo HSC marker Endoglin was tested on ex vivo expanded HSCs. After 10 days of culture, 6,000 Endoglin$^+$ and 24,000 Endoglin$^+$ cells, or 10,000 Lin$^-$Endoglin$^+$ and 10,000 Lin$^-$Endoglin$^+$ cells were transplanted together with $10^5$ CD45.1 competitor cells into lethally irradiated CD45.1 mice (n=4). Peripheral blood cells were analyzed for the presence of CD45.2$^+$ cells in lymphoid and myeloid compartments at 4 weeks and 4 months after transplant. 26% of total cells were Endoglin$^+$ cells (Table 2). Both Endoglin$^+$ and Endoglin$^+$ cells contain portions of the ST-HSC and LT-HSC activities (FIG. 4). The same was true of the Lin$^-$Enodglin$^+$ and Lin$^-$Endoglin$^+$ populations (FIG. 4).

Next the PrP status of cultured HSCs was tested. Whereas PrP+ cells make up only 0.8% of Lin– cells in freshly isolated BM (not shown), this fraction increased substantially to 60% after 10 days of culture (Table 1).

TABLE 1

Expanded cells can rescue lethally irradiated mice

| Survival Cell Number | Fresh | Cultured |
|---|---|---|
| $1 \times 10^4$ | 0/3 | 1/3 |
| $3 \times 10^4$ | 1/3 | 3/3 |
| $1 \times 10^5$ | 3/3 | 3/3 |

Figure 5:
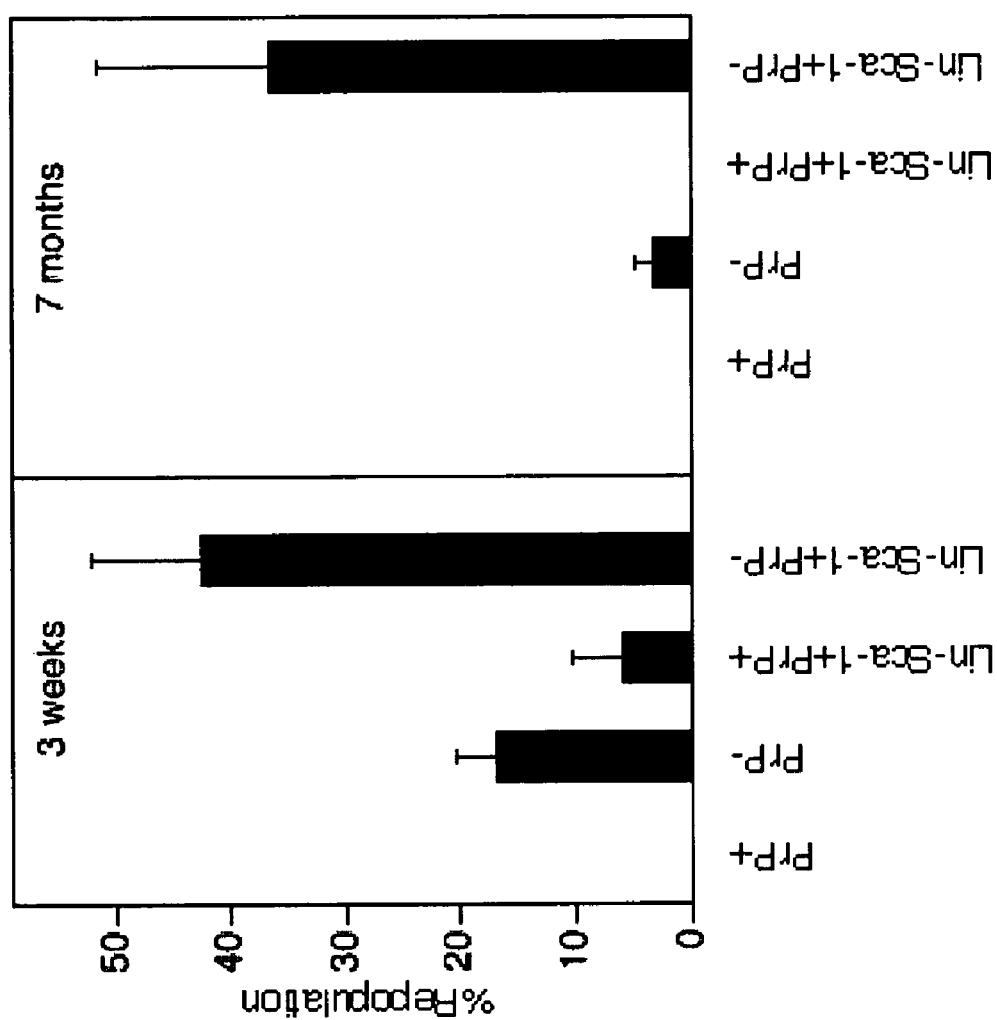
FIG. 5 is a chart showing % repopulation at 3 weeks and 7 months after transplant, demonstrating that ex vivo expanded bone marrow HSCs are PrP$^-$.

PrP$^+$ and PrP$^-$ cells were sorted from the culture and transplanted 10,000 of each with $10^5$ competitors. Surprisingly, all of the ST- and LT$^-$HSC repopulating activity resided in PrP$^-$ but not in the PrP$^+$ fraction (FIG. 5). 3,000 cultured Lin$^-$PrP$^+$ and Lin$^-$ PrP$^+$ cells were competitively transplanted; again, Lin$^-$ PrP$^-$ but not Lin$^-$ PrP$^+$ cells contained all the repopulating LT-potential of these cultured cells 10,000 PrP$^+$ and PrP$^+$ cells cultured for 10 days, or 3,000 Lin$^-$PrP$^+$ and Lin$^-$PrP$^-$ cells cultured for 4 days were transplanted together with $10^5$ CD45.1 competitor cells into lethally irradiated CD45.1 mice (n=4). Peripheral blood cells were analyzed for the presence of CD45.2$^+$ cells in lymphoid and myeloid compartments at 3 weeks and 7 months after transplant (FIG. 5). This is different from freshly isolated bone marrow cells, in which all the HSC activity is in the PrP+ cells. It suggests that HSCs must have diminished their surface expression of PrP during the expansion in culture.

Figure 6:
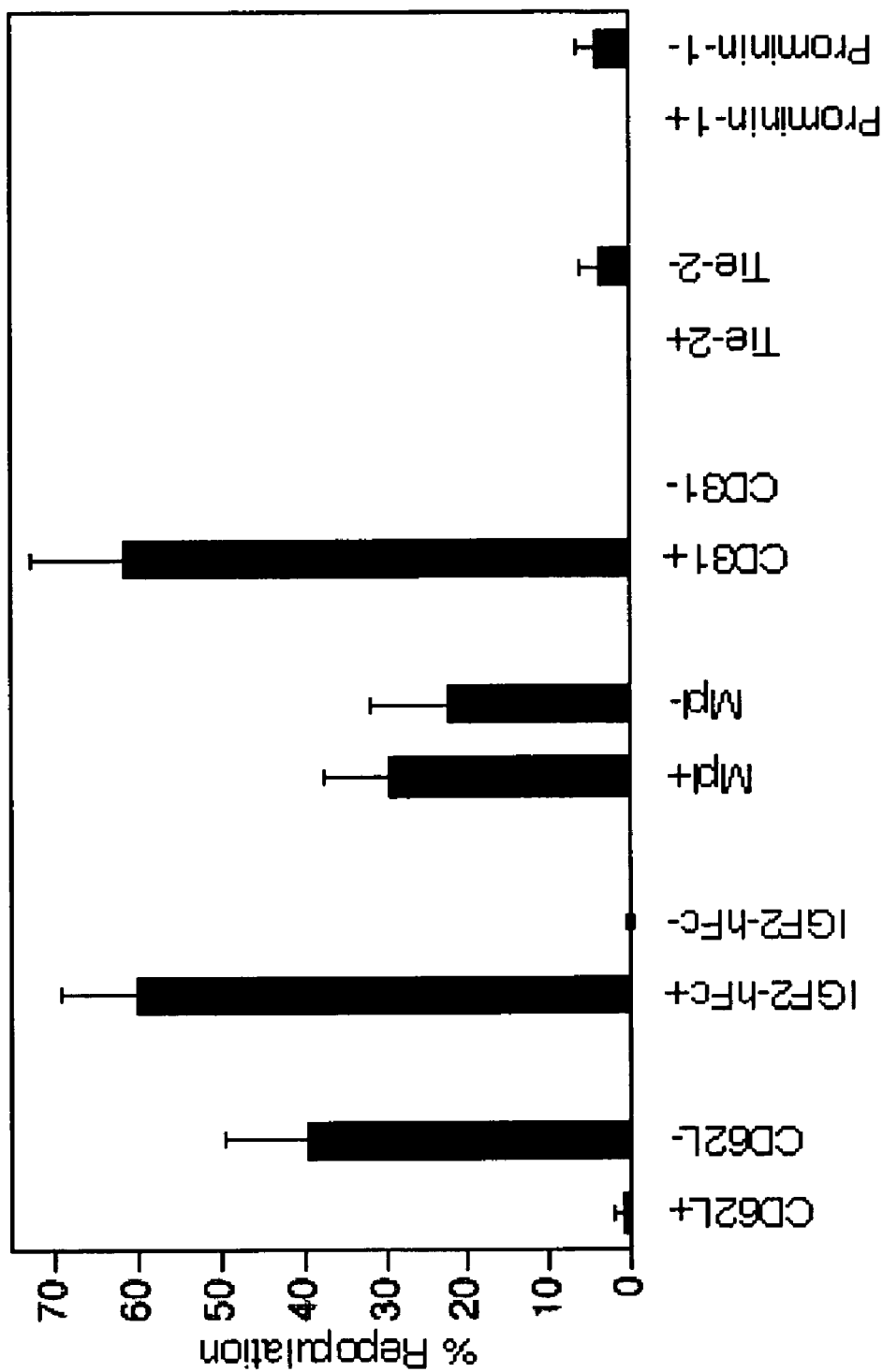
FIG. 6 is a chart showing % repopulation from transplanted cells having the indicated phenotype demonstrating that ex vivo expanded bone marrow HSCs are Tie-2$^-$ prominin-1$^-$.

FIG. 6 demonstrates that expanded HSCs do not express the in vivo HSC markers Tie-2 or prominin-1. The positive and negative fractions of cultured cells were sorted after immunostaining with antibodies against CD62L, Mpl, CD31, Tie-2, or prominin-1, or after incubation with IGF2-hFc followed by competitive transplantation. The LT-repopulating activity was found in the CD62L−, IGF2-hFc+, CD31+, Tie-2−, and prominin-1− fractions. Both Mpl+ and Mpl− cells contained LT-HSC activities. The engraftment of CD34 and CD38 positive and negative cells after culture was also tested. More than 90% of cells are CD34− or CD38−. These data suggested that repopulating cultured BM LT-HSCs are contained in the Sca-1+, Kit+, CD31+, IGF2-hFc+, PrP−, Tie-2−, prominin-1−, CD38−, and CD62L− population.

These experiments demonstrate that the above in vivo HSC markers do not necessarily serve as markers for cultured HSCs; therefore, the expression of additional in vivo HSC markers and cell surface proteins on expanded cells was tested, including IGF2 receptors, Mpl, CD31, Flk1, CD34, CD38, CD62L, CD43, CD44, CD49D, CD49E, CD11A, CXCR4, and CD24 (Table 2). The majority of the 10 day cultured cells expressed Flk1, CD43, CD44, CD49D, CD49E, CD11a, CXCR4, and CD24. By contrast, 50% of cultured cells were CD62L+, 40% were IGF2-hFc+, 44% were Mpl+, 55% were CD31+, 8% were CD34+. The positive and negative fractions of cultured cells were sorted after immunostaining with antibodies against CD62L, Mpl, CD31, CD34, or CD38, or after incubation with IGF2-hFc that bind to cells with receptors against IGF-2. The repopulating activity was found in the CD62L−, IGF2-hFc+, CD31+, CD34−, or CD38− fractions. Both Mpl+ and Mpl− cells contained HSC activities (FIG. 6). These data suggested that the repopulating cultured BM HSCs were contained in the Lin− Sca-1+Kit+ CD31+IGF2-hFc+PrP−Tie-2−prominin-1−  CD34−CD38− CD62L− population.

Figure 7B:
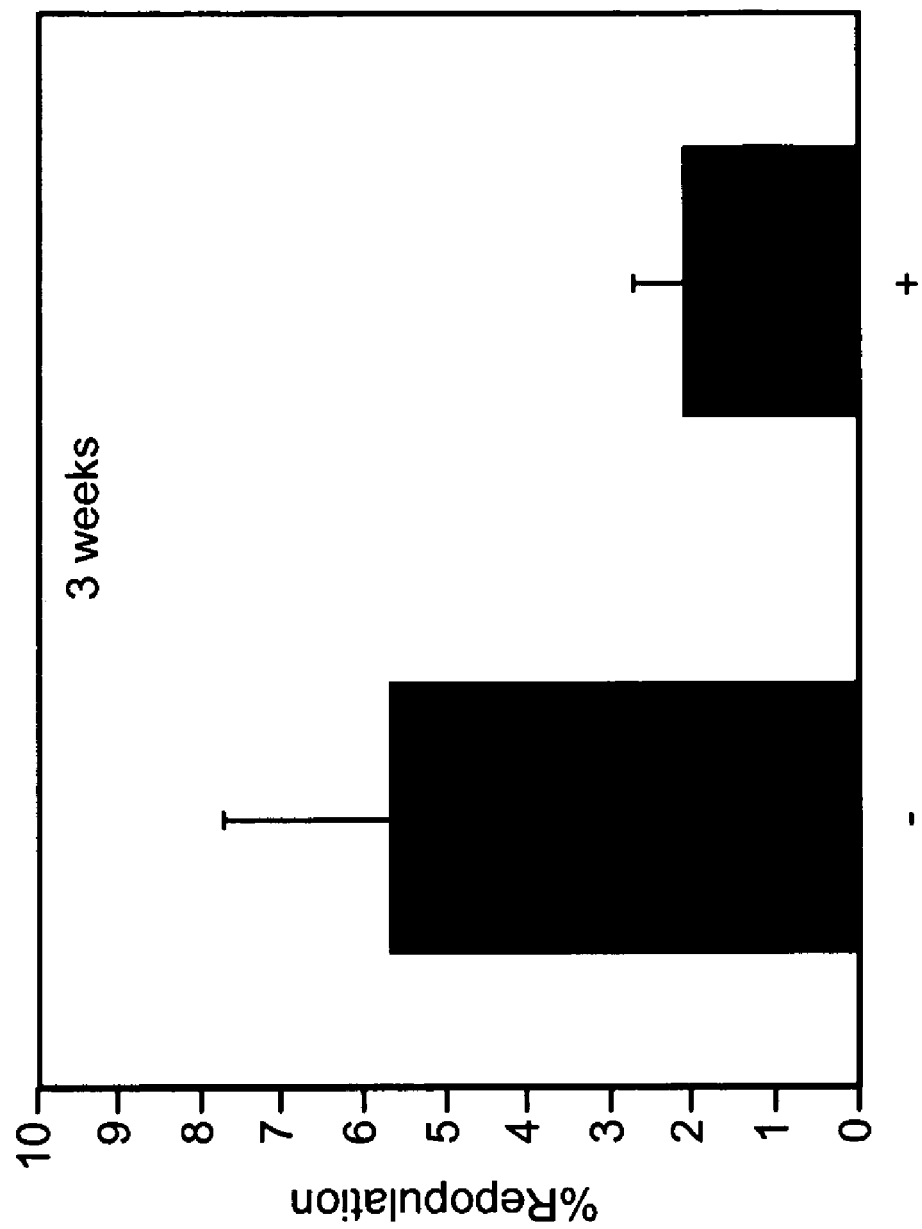
FIG. 7B shows a chart of % repopulation with Lin$^-$Sca-1$^+$PrP$^-$CD62L$^-$IGF-2 receptor$^-$ cells 3 weeks after transplant, demonstrating that cultured Lin$^-$Sca-1$^+$PrP$^-$CD62L$^-$ IGF-2receptor$^+$ cells repopulated mice.

Because almost all Sca-1+ cells were also Kit+ (FIG. 3A), and the populations defined as CD31+, Tie-2−, prominin-1−, or CD34− cells contained the majority of the cells and could not provide further enrichment (Table 2), we tested whether Lin−Sca-1+IGF2-hFc+PrP−CD62L− cells (FIG. 7A) were enriched HSCs that were capable of engrafting recipients in competitive repopulation. 10 day cultured bone marrow cells were stained with IGF2-hFc, followed by anti-human IgG1 Fc-PE, anti-PrP, anti-mouse-PE/CY5.5, a cocktail of biotinylated lineage-specific antibodies, and streptavidin-PE/CY5.5, anti-Sca-1-FITC, and anti-CD62L-APC. The Lin− PrP−PI− cells were gated to show the surface expression of Sca-1/CD62L (left) and Lin− PrP+ Sca-1+CD62L− cells were gated to show the binding to IGF2-hFc (right). FIG. 8B shows that cultured Lin−Sca-1+PrP−CD62L−IGF2-hFc+ cells repopulated mice. After 10 days of culture, 800 sorted CD45.2 Lin−Sca-1+PrP−CD62L−IGF2-hFc+ and 1,600 CD45.2 Lin−Sca-1+PrP−CD62L−IGF2-hFc− cells were transplanted together with 2×10$^5$ CD45.1 competitor cells into lethally irradiated CD45.1 mice (n=4). Peripheral blood cells were analyzed for the presence of CD45.2+ cells in lymphoid and myeloid compartments at 3 weeks after transplant. 800 Lin−Sca-1+PrP−CD62L− IGF2-hFc+ provided 5.7% chimerism while 1,600 Lin−Sca-1+PrP−CD62L− IGF2-hFc− cells showed 2.1% chimerism (FIG. 7B) 3 weeks post-transplant. Therefore, Lin−Sca-1+PrP−CD62L− IGF2-hFc+ cells enriched ex vivo expanded BM HSC activity. Because the enrichment provided by Lin−PrP− (17.9%×60% of total cells) was about 10 fold, Sca-1+CD62L− (110% of Lin−PrP− cells) provided a further 10 fold enrichment, and IGF2-hFc+ (3% of Lin−PrP−Sca-1+ CD62L− cells) enriched another 30 fold, the total enrichment of cultured HSC activity was ~3000 fold.

TABLE 2

Expression of surface proteins on ex vivo expanded BM cells

| | Protein | | | | | | | | | | |
|---|---|---|---|---|---|---|---|---|---|---|---|
| | Sca-1 | c-Kit | PrP | Endoglin | Tie-2 | AC 133 | CD31 | CD62L | CD34 | IGF2-hFc | MPL |
| % of positive cells | 33 | 34 | 50 | 26 | 5.7 | 0.3 | 55 | 50 | 8 | 40 | 84 |
| % of Lin-cells | 35 | 33 | 60 | 20 | 0.7 | 0.6 | 98 | 51 | 0.1 | 12 | 44 |

| | Protein | | | | | | | | |
|---|---|---|---|---|---|---|---|---|---|
| | Flk1 | CD43 | CD44 | CD49D | CD49E | CD11A | CXCR4 | CD24 | CD38 |
| % of positive cells | 80 | 97 | 99 | 93 | 97 | 98 | 71 | 92 | 5 |

A simple and robust culture system for expanding HSCs is provided herein. As a result of the present invention, LT-HSCs can be significantly expanded in culture without causing earlier senescence. Importantly, the expansion of LT-HSCs exceeded the expansion of differentiated cells. Although the surface proteins on cultured HSCs significantly differ from that of in vivo HSCs, ex vivo expanded HSCs were capable of engrafting BM efficiently. A more than 3000 fold enrichment of HSCs has been achieved using our FACS based isolation method.

One component of the culture system provided herein is the combination of low levels of four cytokines (SCF, TPO, IGF-2, and FGF-1) in serum-free medium. Other factors were tested including FGF-2 and Wnt 3a, which did not show further enhancement of HSC activity after being added into the cocktail mixture. Without wishing to be bound by theory, in the initial phase of the culture, the presence of low concentrations of the factors in the serum-free medium may ensure that only HSCs but not their differentiated progenies are directly bound and co-stimulated by multiple positive signals for survival and self-renewal. Since HSCs in both total bone marrow cells and purified HSCs can be expanded, it seems that HSCs are the primary target of these cytokines. After HSCs expansion, differentiated cell numbers increase and these cells may also produce factors that stimulate HSC self-renewal. The utility of the method of the present invention is evident by the presence of Kit (SCF receptor), IGF2 receptors on all cultured HSCs, and Mpl (TPO receptor) on some cultured HSCs.

The expression of surface proteins on ex vivo expanded HSCs has not been systematically investigated before. Relative to the status of in vivo HSCs, the expression of surface proteins on cultured HSCs can be divided into three groups. The first group consists of proteins expressed on in vivo HSCs or progenitors and retained on expanded HSCs. Included in this group are Kit, Sca-1, CD31, IGF2 receptors. The second group, which includes in vivo HSC markers such as Endoglin, PrP, Tie-2, Mpl, CD38, or prominin-1 (AC 133 in humans), is defined by the loss of some or all expression on ex vivo expanded HSCs. The third group, proteins not expressed on in vivo HSCs and still absent on cultured HSCs, includes CD34 and CD62L.

The in vivo HSC markers Kit, Sca-1, IGF2 receptors, and CD31 are still expressed on ex vivo expanded HSCs. This category also possibly includes some cell surface adhesion molecules or chemokine receptor CD43, CD44, CD49D, CD49E, and CXCR4, which were shown previously to be found on in vivo primitive stem cell or progenitors. This result suggests that HSCs are still in $Lin^-Sca-1^+Kit^+$ fractions after culture. Although this fraction is greatly expanded and its majority may be progenitors and differentiated cells, it is still useful for enrichment of ex vivo expanded HSCs, especially in combination with other markers. In contrast, most cultured cells express all the rest of the above proteins except Kit and Sca-1. Hence they do not provide further enrichment of cultured HSCs.

It is surprising that three in vivo HSC markers, PrP, Tie-2, and prominin-1 (AC133), completely lose their surface expression on HSCs after culture. PrP is expressed on all in vivo LT-HSCs and is involved in their self-renewal. Without wishing to be bound by theory, this regulation of HSCs may be dependent on the bone marrow microenvironment. Similar to Tie-2, PrP also may maintain the quiescent state of BM HSCs. Because PrP was no longer expressed on cultured HSCs, PrP and Tie-2 may be sensors of signaling in the bone marrow microenvironment and may play a role in the regulation of HSCs. Once HSCs are removed from the bone marrow, PrP and Tie-2 may be downregulated and eventually lost on the surface of HSCs. This is consistent with the observation that PrP is expressed on almost all bone marrow $Ter119^+$ erythroid cells, but is no longer found on $Ter119^+$ cells in the peripheral blood. It will be very interesting to study the PrP or Tie-2 status on HSCs in the recipient BM after these cultured $PrP^-$ stem cells are transplanted. If PrP or Tie-2 is functionally important for HSCs in bone marrow, its surface expression on engrafted HSCs should be restored.

Unlike PrP, Tie-2, and prominin-1 (AC133), which completely lose surface expression on cultured HSCs, the in vivo stem cell markers Endoglin and Mpl retain their expression in some but not all of cultured HSCs. Since the functions of these proteins on HSCs are not fully understood, several possibilities exist. Possibilities include: 1) that the cultured $Endo^+$ and – HSCs represent different original stem cell populations, 2) that the + and – stem cells reflect different quiescent states, or 3) that the change of Endoglin or Mpl on HSCs reflects downregulation due to their loss of function in the culture environment.

The reversed expression of CD34 in quiescent and activated HSCs was reported (19). In our ex vivo expansion system, we observed consistency in the status of CD34–, it is negative on both in vivo and cultured HSCs. CD62L is also not expressed on either in vivo HSCs or cultured HSCs.

The expression of surface proteins on cultured HSCs is so different from in vivo HSCs, no obvious logic summarizes this change. Generally, ex vivo expanded HSCs reside in a majority of population. For instance, they are in $CD31^+$ that is 98% of cultured $Lin^-$ cells, and in $Tie-2^-$, $AC 133^-$, or $CD34^-$, which are more than 99% of cultured $Lin^-$ cells (Table 1). This makes it difficult to make use of these markers for enriching cultured HSCs.

The change of surface proteins in cultured HSCs is consistent with the general observation that cultured HSCs have altered homing ability. HSCs expanded in the culture system provided herein may indeed have impaired homing to BM, because a relatively large number of cultured cells was needed, for instance, 800 $Lin^-Sca-1^+PrP^-CD62L^-$ $IGF2-hFc^+$ cells, to efficiently engraft recipients. This can possibly be explained by a decreased homing ability in highly enriched expanded HSCs.

This culture system and the study of phenotype of cultured HSCs have wide applications. Use of a combination of low levels of cytokines that directly stimulate HSCs in a serum-free medium is applicable to expanding human HSCs for transplantation. This culture system is also useful for introducing genetic materials to HSCs, which requires the culture of HSCs without losing their activity. The expanded HSC activity and the 10 day culture time is ideal for drug selection of genetic modified HSCs. The methods for identifying HSCs provided herein will be valuable for stem cell purification and analysis, and will be particularly useful for developing a screening system for the regulation of HSC activities, either by means of chemical genetics, cDNA libraries or RNAi libraries.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The references cited herein and throughout the specification are incorporated by reference.

We claim:

1. A method for expanding hematopoietic stem cells ex vivo, comprising culturing a population of cells that includes hematopoietic stem cells in a medium comprising insulin-like growth factor-2 (IGF-2) and at least one factor selected from the group consisting of fibroblast growth factor (FGF), thrombopoietin (TPO), and stem cell factor (SCF), under conditions sufficient for expansion of the hematopoietic stem cells, thereby expanding hematopoietic stem cells ex vivo.

2. The method of claim 1, wherein at least two factors from the group are present in the medium.

3. The method of claim 1, wherein at least three factors from the group are present in the medium.

4. The method of claim 1, wherein the FGF is FGF-1.

5. The method of claim 1, wherein the medium comprises IGF-2, FGF-1, SCF, and TPO.

6. The method of claim 1, wherein the IGF-2 is present at a concentration of about 20 ng/ml.

7. The method of claim 1, wherein FGF is present at a concentration of about 10 ng/ml.

8. The method of claim 1, wherein TPO is present at a concentration of about 20 ng/ml.

9. The method of claim 1, wherein SCF is present at a concentration of about 10 ng/ml.

10. The method of claim 1, wherein the cells are cultured for about two weeks.

11. The method of claim 1, wherein said population of cells comprises total bone marrow.

12. The method of claim 1, wherein said population of cells comprises a sub-population of total bone marrow cells.

13. The method of claim 1, wherein the expanded hematopoietic stem cells are at least about 8-fold enriched for long term hematopoietic stem cells.

14. The method of claim 1, wherein said culture medium comprises serum-free medium.

15. The method of claim 1, further comprising the step of separating cells from the population of cells.

16. The method of claim 15, wherein said separating is performed after culturing said population of cells.

17. The method of claim 15, wherein the step of separating comprises selecting cells that express Kit.

18. The method of claim 17, where the step of separating comprises selecting cells that express IGF-2 receptor.

19. The method of claim 15, wherein the step of separating comprises selecting cells that express Kit and IGF-2 receptor.

20. The method of claim 15, wherein the step of separating comprises selecting cells that do not express at least one negative cell surface marker.

21. The method of claim 20, wherein the step of separating is performed after culturing said population of cells.

22. The method of claim 20, wherein the step of separating comprises selecting cells that do not express Lin.

23. The method of claim 1, further comprising the step of separating cells the population of cells by selecting cells that express at least one positive cell surface marker and that do not express at least one negative cell surface marker.

24. The method of claim 23, wherein the step of separating is performed after culturing said population of cells.

25. The method of claim 23, wherein the method comprises selecting cells that express Kit and that do not express Lin.

26. The method of claim 25, wherein the method comprises selecting cells that express IGF-2 receptor.

27. The method of claim 23, wherein the method comprises selecting cells that express IGF-2 receptor and that do not express Lin.

* * * * *